US010889536B1

(12) United States Patent
Boone et al.

(10) Patent No.: US 10,889,536 B1
(45) Date of Patent: Jan. 12, 2021

(54) ENOL ETHERS

(71) Applicant: Eastman Chemical Company, Kingsport, TN (US)

(72) Inventors: Matthew Allen Boone, Kingsport, TN (US); Stephanie Kay Clendennen, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/560,161

(22) Filed: Sep. 4, 2019

(51) Int. Cl.
*C07C 43/00* (2006.01)
*C07C 43/16* (2006.01)
*C07C 43/162* (2006.01)
*C07C 69/533* (2006.01)
*C07C 69/76* (2006.01)
*C07C 43/178* (2006.01)

(52) U.S. Cl.
CPC ............ *C07C 43/16* (2013.01); *C07C 43/162* (2013.01); *C07C 43/1785* (2013.01); *C07C 69/533* (2013.01); *C07C 69/76* (2013.01)

(58) Field of Classification Search
CPC .... C07C 43/16; C07C 43/162; C07C 43/1785
See application file for complete search history.

(56) References Cited

U.S. PATENT DOCUMENTS

| 2,578,724 | A | | 12/1951 | Mertzweiller |
| 4,839,413 | A | | 6/1989 | Kiehlbauch et al. |
| 4,927,876 | A | | 5/1990 | Coogan et al. |
| 4,939,233 | A | | 7/1990 | Jenkins et al. |
| 4,946,932 | A | | 8/1990 | Jenkins |
| 5,053,556 | A | * | 10/1991 | Ohnishi .................. C07C 41/01 568/579 |
| 5,137,961 | A | | 8/1992 | Goos et al. |
| 5,247,040 | A | | 9/1993 | Amick et al. |
| 5,296,530 | A | | 3/1994 | Bors et al. |
| 5,484,849 | A | | 1/1996 | Bors et al. |
| 6,451,380 | B1 | | 9/2002 | Speece, Jr. et al. |
| 6,743,748 | B2 | | 6/2004 | Mizuno et al. |
| 7,208,545 | B1 | | 4/2007 | Brunner et al. |
| 9,932,486 | B1 | | 4/2018 | Cogar et al. |
| 2009/0035696 | A1 | * | 2/2009 | Matsuoka ............. G03F 7/0007 430/281.1 |
| 2009/0076311 | A1 | | 3/2009 | Sato et al. |
| 2012/0289721 | A1 | | 11/2012 | End et al. |
| 2015/0239816 | A1 | | 8/2015 | Zaragoza Doerwald et al. |

FOREIGN PATENT DOCUMENTS

EP          0 492 847 A2   7/1992
WO    WO 2007/094922 A2   8/2007

OTHER PUBLICATIONS

Trost et al. A Model for Asymmetric Induction in the Diels-Alder Reaction. Journal of the American Chemical Society, vol. 102, 7595-7596. (Year: 1980).*

Co-pending U.S. Appl. No. 16/559,842, filed Sep. 4, 2019; Boone.
Co-pending U.S. Appl. No. 16/559,871, filed Sep. 4, 2019; Boone.
Co-pending U.S. Appl. No. 16/559,887, filed Sep. 4, 2019; Boone.
Co-pending U.S. Appl. No. 16/559,912, filed Sep. 4, 2019; Boone.
Co-pending U.S. Appl. No. 16/559,897, filed Sep. 4, 2019; Boone.
Co-pending U.S. Appl. No. 16/559,880, filed Sep. 4, 2019; Boone et al.
Co-pending U.S. Appl. No. 16/559,859, filed Sep. 4, 2019; Boone et al.
Co-pending U.S. Appl. No. 16/560,146, filed Sep. 4, 2019; Boone et al.
Co-pending U.S. Appl. No. 16/559,977, filed Sep. 4, 2019; Boone.
Co-pending U.S. Appl. No. 16/559,988, filed Sep. 4, 2019; Boone et al.
ASTM D1544; Standard Test Method for Color of Transparent Liquids (Gardner Color Scale).
ASTM D2354-10$^{e1}$; Standard Test Method for Minimum Film Formation Temperature (MFFT) of Emulsion Vehicles.
ASTM D4946; Standard Test Method for Blocking Resistance of Architectural Paints.
ASTM D6886; Standard Test Method for Determination of the Weight Percent Individual Volatile Organic Compounds in Waterborne Air-Dry Coatings by Gas Chromatography.
Burczyk, B. et al.; "Relations between chemical structure and surface activity I: Synthesis and properties of aqueous solutions of acetals formed from aliphatic aldehydes and monoalkyl ethers of ethylene glycols;" Tenside Detergents; 15(2); 1978; pp. 68-71.
Burczyk, B. et al.; "Surface Properties of Selected Linear and Cyclic Acetals;" Tensioactivos: Biodegradabilidad, Fis.-Quim. Apl., Jorn. Com. Esp. Deterg.; 11$^{th}$; 1980; pp. 581-601.
Cohen, R. et al.; "Foam stabilizing properties of linear acetals containing oxyethylene units in their molecules;" Tenside Detergents; 18 (4); 1981; pp. 202-205.
Duchene, A. et al.; "Alxoxyméthyltributylétains précurseurs d'alcoxyméthyllithiums : application à la synthèse de monoéthers d'α-glycols et à l'homologation de cétones en aldéhydes;" Bulletin De La Societe Chimique De France; 1985; No. 5; pp. 787-792.
Getzkin, AJ. et al.; "Synthesis of Some Symmetrical Aldehyde Glycol Monoether Acetals;" Journal of the American Pharmaceutical Association, Scientific Edition; 49; 1960; pp. 746-750.
Kanno, T. et al.; "Oxygenation of Aromatic Vinyl Ethers. A Noticeable Formation of Epoxides and Reaction Mechanism;" Bull. Chem. Soc. Jpn.; 54; 1981; pp. 2330-2336.
Moszner, N. et al.; "Reaction behavior of monomeric β-ketoesters. 2. Synthesis, characterization and polymerization of methacrylate group containing enamines;" Polymer Bulletin; 32; pp. 419-426; (1994).
Presidential Green Chemistry Challenge: 2005 Designing Greener Chemical Award; Archer Daniels Midland Company; Archer RC™: A Nonvolatile, Reactive Coalescent for the Reduction of VOCs in Latex Paints; United States Environmental Protection Agency; Accessed via the web on Jun. 6, 2018; https://www.epa.gov/greenchemistry/presidential-green-chemistry-challenge-2005-designing-greener-chemicals-award.

(Continued)

*Primary Examiner* — Sikarl A Witherspoon
(74) *Attorney, Agent, or Firm* — Matthew W. Smith

(57) ABSTRACT

Disclosed are enol ethers compounds. The enol ethers exhibit low volatile organic content and are useful in a variety of chemical applications. The enol ethers can be used in applications as diluents, wetting agents, coalescing aids, paint additives and as intermediates in chemical processes. The enol ethers also have particular utility as film-hardening additives in coating formulations.

22 Claims, No Drawings

(56) References Cited

OTHER PUBLICATIONS

Robinson, M. et al.; "Epoxide ring-opening and Meinwald rearrangement reactions of epoxides catalyzed by mesoporous aluminosilicates;" Organic & Biomolecular Chemistry; 2009; 7; pp. 2559-2564.
Safa, K. et al.; "1,4-bis[2,2-bis(trimethylsilyl)ethenyl]benzene: Regioselective ring opening of its a,B-eposybix(silane) with some nucleophiles;" Journal of Organometallic Chemistry; 694; 20019; pp. 1907-1911.
Smith, O.W. et al.; "New vinyl ester monomers for emulsion polymers;" Progress in Organic Coatings; 22; 1993; pp. 19-25.
Sokolowski, A. et al.; "Acetals and Ethers. Part IV*. Synthesis of Acetals from Aliphatic Aldehydes and Monoalkyl Ether of Ethylene Glycols;" Polish Journal of Chemistry (formerly Roczniki Chemii); 53(4); 1979; pp. 905-912.
Sokolowski, A. et al.; "Statistical Evaluation of the Influence of Linear Acetal Structures on Their Adsorption at the Aqueous Solution-Air Interface;" Comunicaciones presentadas a las XII Jornadas del Comite Espanol de la Detergencia; Asociacion De Investigacion De Detergentes, TENS; 1981; pp. 491-507.
USPTO Office Action dated Apr. 6, 2020 received in co-pending U.S. Appl. No. 16/559,842.
USPTO Notice of Allowance dated Nov. 1, 2019 received in co-pending U.S. Appl. No. 16/559,977.
USPTO Notice of Allowance dated Dec. 10, 2019 received in co-pending U.S. Appl. No. 16/559,977.
USPTO Notice of Allowance dated Nov. 1, 2019 received in co-pending U.S. Appl. No. 16/559,988.
USPTO Notice of Allowance dated Dec. 11, 2019 received in co-pending U.S. Appl. No. 16/559,988.
Kluge et al.; "Phosphonate Reagents for the Synthesis of Enol Ethers and One-Carbon Homologation to Aldehydes;" J. Org. Chem.; vol. 44; No. 26; 1979; pp. 4847-4852.
USPTO Office Action dated Jun. 1, 2020 received in co-pending U.S. Appl. No. 16/559,897.
USPTO Office Action dated Jun. 10, 2020 received in co-pending U.S. Appl. No. 16/559,871.
USPTO Office Action dated Jun. 10, 2020 received in co-pending U.S. Appl. No. 16/559,912.
USPTO Notice of Allowance dated Jun. 24, 2020 received in co-pending U.S. Appl. No. 16/559,887.

* cited by examiner

ENOL ETHERS

FIELD OF THE INVENTION

This application relates to chemistry generally. This application also relates to enol ethers and processes for preparing enol ethers.

BACKGROUND OF THE INVENTION

Enol ethers are useful in a variety of chemical applications such as diluents, wetting agents and paint additives and as intermediates in chemical processes. Diluents, wetting agents and paint additives often are volatile and evaporate into the atmosphere during use. For example, coalescing aids lower the glass transition temperature (Tg) of the latex polymer and as the paint dries, the polymers that have been softened by the coalescing aid are allowed to flow together and form a film after the water has left the system. Coalescing aids that are volatile evaporate out of the film. This allows the polymer to return to the original Tg thereby giving harder films for better block and print resistant coatings. Due to environmental concerns, the use of volatile materials such as paint additives, diluents, wetting agents and coalescing aids are increasing undesirable.

As a result, there is a need for materials that can be used as diluents, wetting agents, and paint additives that exhibit low volatility.

In particular, there is a need for paint additives that facilitate the low temperature coalescence of latex particles to form a continuous film, even at application temperatures below the latex polymer $T_g$, while still resulting in a film without compromising hardness, block or print resistance, scrub resistance, weatherability or solvent resistance and which exhibit low volatility. In particular, a need exists for waterborne coating compositions which may be formulated as a single, shelf-stable composition but which exhibit efficient film formation imparting desired properties to the resulting coating.

Other beneficial features of a good coalescing aid include low water solubility, ease of addition to paint formulations, compatibility with multiple formulations, high coalescing efficiency, low freezing point, low foaming and good hydrolytic stability. A good coalescing aid will be compatible with most latex polymers, is easily added to formulations, has low volatility and odor, and provides good color development properties.

SUMMARY OF THE INVENTION

The present application discloses a compound according to Formula I:

$$A=\diagdown_{O-R^{1a}} \quad \text{I}$$

wherein:

A is (a)

$$\underset{R^3}{\overset{R^2}{\diagdown}}{**},$$

wherein ** indicates the point of attachment, or (b) $(C_{3-8})$cycloalkyl;

$R^{1a}$ $$\diagdown\diagdown\diagdown{\diagup}{O{\left[\diagdown{\diagup}O\right]}_n}R^4;$$

$R^2$ is $(C_{2-12})$alkyl;

$R^3$ is $(C_{1-12})$alkyl;

$R^4$ is hydrogen, $(C_{1-12})$alkyl, $(C_{2-12})$alkenyl, or $-C(O)R^5$;

$R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;

each $R^6$ is $(C_{1-4})$alkoxy, or oxo; and n is an integer from 1 to 15.

The present application also discloses a compound according to Formula II:

$$R^{1b}-O\diagup{=\!A\!=}\diagdown O-R^{1a} \quad \text{II}$$

wherein:

A is $(C_{3-8})$cycloalkyl;

$R^{1a}$ and $R^{1b}$ are independently $$\diagdown\diagdown\diagdown{\diagup}{O{\left[\diagdown{\diagup}O\right]}_n}R^4;$$

each $R^4$ is independently $(C_{1-12})$alkyl, or $-C(O)R^5$;

each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;

each $R^6$ is $(C_{1-4})$alkoxy, or oxo; and each n is independently an integer from 1 to 15.

The present application also discloses a compound according to Formula III:

$$A=\diagdown_{O-R^{1c}}\diagup=A \quad \text{III}$$

wherein:

each A is independently (a)

$$\underset{R^3}{\overset{R^2}{\diagdown}}{**},$$

wherein ** indicates the point of attachment, or (b) $(C_{3-8})$cycloalkyl;

$R^{1c}$ is $$\diagdown\diagdown\diagdown{\diagup}{O{\left[\diagdown{\diagup}O\right]}_n}\diagdown\diagdown;$$

each $R^2$ is independently $(C_{2-12})$alkyl;

each $R^3$ is independently $(C_{1-12})$alkyl; and n is an integer from 1 to 15.

The present application also discloses compositions made from the compounds according to Formula I, II, or III, and processes for preparing enol ethers.

DETAILED DESCRIPTION

Definitions

In this specification and in the claims that follow, reference will be made to a number of terms, which shall be defined to have the following meanings.

"Alkyl" means an aliphatic hydrocarbon. The alkyl can specify the number of carbon atoms, for example $(C_{1-5})$ alkyl. Unless otherwise specified, the alkyl group can be unbranched or branched. In one embodiment, the alkyl group is branched. In one embodiment, the alkyl group is unbranched. Non-limiting examples of alkanes include methane, ethane, propane, isopropyl (i.e., branched propyl), butyl, and the like.

"Alkenyl" means an aliphatic hydrocarbon with one or more unsaturated carbon-carbon bonds. The alkenyl can specify the number of carbon atoms, for example $(C_{2-12})$ alkenyl. Unless otherwise specified, the alkyl group can be unbranched or branched. In one embodiment, the alkyl group is branched. In one embodiment, the alkyl group is unbranched. Non-limiting examples of alkanes include ethenyl, propenyl, butenyl, hexa-3,5-dienyl, and the like.

"Alcohol" means a chemical containing one or more hydroxyl groups.

"Aldehyde" means a chemical containing one or more —C(O)H groups.

"Cycloalkyl" means a cyclic hydrocarbon compound. The cycloalkyl can specify the number of carbon atoms in ring system, for example $(C_3-8)$cycloalkyl. Non-limiting examples of cycloalkyl include cyclopropyl, cyclobutyl, cyclohexyl, and cyclooctyl.

"Aryl" means a ring system made up carbon atoms that has at least one ring that is aromatic. The carbon units making up the aryl ring may be specified, for example 5- to 9-membered aryl. Non-limiting examples of aryl include phenyl, naphthyl, 2,3-dihydro-1H-indene, and 1,2,3,4-tetrahydronaphthalene.

Values may be expressed as "about" or "approximately" a given number. Similarly, ranges may be expressed herein as from "about" one particular value and/or to "about" or another particular value. When such a range is expressed, another aspect includes from the one particular value and/or to the other particular value. Similarly, when values are expressed as approximations, by use of the antecedent "about," it will be understood that the particular value forms another aspect.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

"Chosen from" as used herein can be used with "or" or "and." For example, Y is chosen from A, B, and C means Y can be individually A, B, or C. Alternatively, Y is chosen from A, B, or C means Y can be individually A, B, or C, or a combination of A and B, A and C, B and C, or A, B, and C.

Composition of Matter

The present application discloses a compound according to Formula I:

wherein: A is (a)

wherein ** indicates the point of attachment, or (b)$(C_{3-8})$ cycloalkyl; $R^{1a}$ is

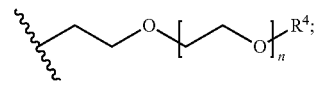

$R^2$ is $(C_{2-12})$alkyl; $R^3$ is $(C_{1-12})$alkyl ; $R^4$ is hydrogen, $(C_{1-12})$alkyl, $(C_{2-12})$alkenyl, or —C(O)$R^5$; $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; each $R^6$ is $(C_{1-4})$alkoxy, or oxo; and n is an integer from 1 to 15.

In one embodiment, A is

wherein ** indicates the point of attachment.

In one class of this embodiment, $R^2$ is ethyl, propyl, butyl, pentyl, heptyl, hexyl, heptyl, octyl, nonyl, or decyl. In one subclass of this class, $R^3$ is methyl, ethyl, propyl, butyl, pentyl, heptyl, hexyl, heptyl, octyl, nonyl, or decyl. In one sub-subclass of this subclass, n is an integer from 1 to 4.

In one class of this embodiment, $R^2$ is propyl, butyl, or pentyl; and $R^3$ is methyl or ethyl. In one subclass of this class, n is an integer from 1 to 4.

In one embodiment, A is $(C_{3-8})$cycloalkyl. In one class of this embodiment, n is an integer from 1 to 4. In one subclass of this class, n is an integer from 1 to 4. In one sub-subclass of this subclass, $R^4$ is hydrogen. In one sub-subclass of this subclass, $R^4$ is $(C_{1-12})$alkyl. In one sub-sub-subclass of this sub-subclass, $R^4$ is ethyl, propyl, or butyl. In one sub-subclass of this subclass, $R^4$ is $(C_{2-12})$alkenyl.

In one sub-subclass of this subclass, $R^4$ is —C(O)$R^5$. In one sub-sub-subclass of this sub-subclass, $R^5$ is $(C_{1-12})$alkyl unsubstituted or substituted by $R^6$. In one sub-sub-subclass of this sub-subclass, $R^5$ is $(C_{2-12})$alkenyl unsubstituted or substituted by $R^6$. In one sub-sub-subclass of this sub-subclass, $R^5$ is $(C_{3-8})$cycloalkyl. In one sub-sub-subclass of this sub-subclass, $R^5$ is 5- to 9-membered aryl.

In one class of this embodiment, A is cyclobutyl, cyclopentyl, cyclohexyl, cycloheptyl or cyclooctyl. In one subclass of this class, n is an integer from 1 to 4. In one sub-subclass of this subclass, $R^4$ is hydrogen. In one sub-subclass of this subclass, $R^4$ is $(C_{1-12})$alkyl. In one sub-subclass of this sub-subclass, $R^4$ is ethyl, propyl, or butyl. In one sub-subclass of this subclass, $R^4$ is $(C_{1-12})$alkenyl.

In one sub-subclass of this subclass, $R^4$ is —C(O)$R^5$. In one sub-sub-subclass of this sub-subclass, $R^5$ is $(C_{1-12})$alkyl unsubstituted or substituted by $R^6$. In one sub-sub-subclass of this sub-subclass, $R^5$ is $(C_{1-12})$alkenyl unsubstituted or substituted by $R^6$. In one sub-sub-subclass of this sub-subclass, $R^5$ is $(C_{3-8})$cycloalkyl. In one sub-sub-subclass of this sub-subclass, $R^5$ is 5- to 9-membered aryl.

In one class of this embodiment, A is cyclohexyl. In one subclass of this class, n is an integer from 1 to 4. In one sub-subclass of this subclass, $R^4$ is hydrogen. In one sub-subclass of this subclass, $R^4$ is $(C_{1-12})$alkyl. In one sub-subclass of this sub-subclass, $R^4$ is ethyl, propyl, or butyl. In one sub-subclass of this subclass, $R^4$ is $(C_{2-12})$alkenyl.

In one sub-subclass of this subclass, $R^4$ is —C(O)$R^5$. In one sub-sub-subclass of this sub-subclass, $R^5$ is $(C_{1-12})$alkyl unsubstituted or substituted by $R^6$. In one sub-sub-subclass of this sub-subclass, $R^5$ is $(C_1\text{-}12)$alkenyl unsubstituted or substituted by $R^6$. In one sub-sub-subclass of this sub-subclass, $R^5$ is $(C_{3-8})$cycloalkyl. In one sub-sub-subclass of this sub-subclass, $R^5$ is 5- to 9-membered aryl.

In one embodiment, $R^4$ is hydrogen. In one embodiment, $R^4$ is $(C_1\text{-}12)$alkyl.

In one class of this embodiment, $R^4$ is methyl, ethyl, propyl, butyl, pentyl, hexyl, heptyl, octyl, or nonyl. In one class of this embodiment, $R^4$ is ethyl, propyl, or butyl. In one class of this embodiment, $R^4$ is ethyl or butyl. In one embodiment, $R^4$ is $(C_{2-12})$alkenyl.

In one embodiment, $R^4$ is —C(O)$R^5$. In one class of this embodiment, $R^5$ is $(C_{1-12})$alkyl unsubstituted or substituted by $R^6$. In one subclass of this class, $R^5$ is methyl, ethyl, propyl, butyl, pentyl, hexyl, heptyl, octyl, or nonyl. In one subclass of this class, $R^5$ is methyl. In one class of this embodiment, $R^5$ is $(C_{2-12})$alkenyl unsubstituted or substituted by $R^6$.

In one class of this embodiment, $R^5$ is $(C_{3-8})$cycloalkyl. In one subclass of this class, $R^5$ is cyclobutyl, cyclopenyl, cyclohexyl, cycloheptyl, or cyclooctyl. In one subclass of this class, $R^5$ is cyclohexyl.

In one class of this embodiment, $R^5$ is 5- to 9-membered aryl. In one subclass of this class, $R^5$ is phenyl or naphthyl. In one subclass of this class, $R^5$ is phenyl.

In one embodiment, n is an integer from 1 to 2. In one embodiment, n is an integer from 1 to 3. In one embodiment, n is an integer from 1 to 4. In one embodiment, n is an integer from 1 to 5. In one embodiment, n is an integer from 1 to 6. In one embodiment, n is an integer from 1 to 7. In one embodiment, n is an integer from 1 to 8. In one embodiment, n is an integer from 1 to 9. In one embodiment, n is an integer from 1 to 10. In one embodiment, n is 1. In one embodiment, n is 2. In one embodiment, n is 3. In one embodiment, n is 4. In one embodiment, n is 5. In one embodiment, n is 6. In one embodiment, n is 7. In one embodiment, n is 7. In one embodiment, n is 8. In one embodiment, n is 9. In one embodiment, n is 10. In one embodiment, n is 11. In one embodiment, n is 12. In one embodiment, n is 13. In one embodiment, n is 14. In one embodiment, n is 15.

In one embodiment, the compound of formula III has a volatile organic content of less than 50 wt % according to ASTM D6886. In one class of this embodiment, the volatile organic content is less than 30 wt %. In one class of this embodiment, the volatile organic content is less than 10 wt %. In one class of this embodiment, the volatile organic content is less than 5 wt %. In one class of this embodiment, the volatile organic content is less than 3 wt %. In one class of this embodiment, the volatile organic content is less than 2 wt %. In one class of this embodiment, the volatile organic content is less than 1 wt %. In one class of this embodiment, the volatile organic content is less than 0.8 wt %.

The present application also discloses a compound according to Formula II:

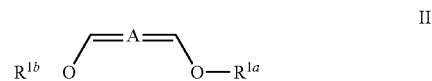

II wherein: A is $(C_{3-12})$alkyl, or $(C_{3-8})$cycloalkyl; $R^{1a}$ and $R^{1b}$ are independently

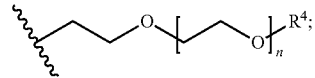

each $R^4$ is independently hydrogen, $(C_{1-12})$alkyl, $(C_{2-12})$alkenyl or —C(O)$R^5$; each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; $R^6$ is $(C_{1-4})$alkoxy, or oxo; and each n is independently an integer from 1 to 15.

In one embodiment, A is cyclobutyl, cyclopentyl, cyclohexyl, cycloheptyl, or cyclooctyl. In one class of this embodiment, each n is an integer from 1 to 3.

In one subclass of this class, each $R^4$ is hydrogen. In one subclass of this class, each $R^4$ is $(C_{1-12})$alkyl. In one sub-subclass of this subclass, each $R^4$ is independently ethyl. In one subclass of this class, each $R^4$ is $(C_{2-12})$alkenyl.

In one subclass of this class, each $R^4$ is —C(O)$R^5$. In one sub-subclass of this subclass, each $R^5$ is $(C_{1-12})$alkyl unsubstituted or substituted by $R^6$. In one sub-subclass of this subclass, each $R^5$ is $(C_{1-12})$alkenyl unsubstituted or substituted by $R^6$. In one sub-sub-subclass of this sub-subclass, each $R^5$ is $(C_{3-8})$cycloalkyl. In one sub-subclass of this sub-subclass, each $R^5$ is 5- to 9-membered aryl.

In one embodiment, A is cyclopropyl. In one class of this embodiment, each n is an integer from 1 to 3. In one subclass of this class, each $R^4$ is hydrogen. In one subclass of this class, each $R^4$ is $(C_{1-12})$alkyl. In one sub-subclass of this subclass, each $R^4$ is independently ethyl. In one subclass of this class, each $R^4$ is $(C_{2-12})$alkenyl.

In one subclass of this class, each $R^4$ is —C(O)$R^5$. In one sub-subclass of this subclass, each $R^5$ is $(C_{1-12})$alkyl unsubstituted or substituted by $R^6$. In one sub-subclass of this subclass, each $R^5$ is $(C_{2-12})$alkenyl unsubstituted or substituted by $R^6$. In one sub-sub-subclass of this sub-subclass, each $R^5$ is $(C_{3-8})$cycloalkyl. In one sub-sub-subclass of this sub-subclass, $R^5$ is 5- to 9-membered aryl.

In one embodiment, A is cyclobutyl. In one class of this embodiment, each n is an integer from 1 to 3. In one subclass of this class, each $R^4$ is hydrogen. In one subclass of this class, each $R^4$ is $(C_{1-12})$alkyl. In one sub-subclass of this subclass, each $R^4$ is independently ethyl. In one subclass of this class, each $R^4$ is $(C_{2-12})$alkenyl.

In one subclass of this class, each $R^4$ is —C(O)$R^5$. In one sub-subclass of this subclass, each $R^5$ is $(C_{1-12})$alkyl unsubstituted or substituted by $R^6$. In one sub-subclass of this subclass, each $R^5$ is $(C_{2-12})$alkenyl unsubstituted or substituted by $R^6$. In one sub-sub-subclass of this sub-subclass, each $R^5$ is $(C_{3-8})$cycloalkyl. In one sub-sub-subclass of this sub-subclass, each $R^5$ is 5- to 9-membered aryl.

In one embodiment, A is cyclopentyl. In one class of this embodiment, each n is an integer from 1 to 3. In one subclass of this class, each $R^4$ is hydrogen. In one subclass of this class, each $R^4$ is $(C_{1-12})$alkyl. In one sub-subclass of this subclass, $R^4$ is independently ethyl. In one subclass of this class, each $R^4$ is $(C_{2-12})$alkenyl.

In one subclass of this class, $R^4$ is —C(O)$R^5$. In one sub-subclass of this subclass, each $R^5$ is $(C_{1-12})$alkyl unsubstituted or substituted by $R^6$. In one sub-subclass of this subclass, each $R^5$ is $(C_{2-12})$alkenyl unsubstituted or substituted by $R^6$. In one sub-sub-subclass of this sub-subclass, each $R^5$ is $(C_{3-8})$cycloalkyl. In one sub-sub-subclass of this sub-subclass, each $R^5$ is 5- to 9-membered aryl.

In one embodiment, A is cyclohexyl. In one class of this embodiment, each n is an integer from 1 to 3. In one subclass of this class, each $R^4$ is hydrogen. In one subclass of this class, each $R^4$ is $(C_{1-12})$alkyl. In one sub-subclass of this subclass, each $R^4$ is independently ethyl. In one subclass of this class, each $R^4$ is $(C_{2-12})$alkenyl.

In one subclass of this class, each $R^4$ is —C(O)$R^5$. In one sub-subclass of this subclass, each $R^5$ is $(C_{1-12})$alkyl unsubstituted or substituted by $R^6$. In one sub-sub-subclass of this sub-subclass, $R^5$ is $(C_{3-8})$cycloalkyl. In one sub-subclass of this subclass, each $R^5$ is $(C_{2-12})$alkenyl unsubstituted or substituted by $R^6$. In one sub-sub-subclass of this sub-subclass, each $R^5$ is 5- to 9-membered aryl.

In one embodiment, A is cycloheptyl. In one class of this embodiment, each n is an integer from 1 to 3. In one subclass of this class, each $R^4$ is hydrogen. In one subclass of this class, each $R^4$ is $(C_{1-12})$alkyl. In one sub-subclass of this subclass, each $R^4$ is independently ethyl. In one subclass of this class, each $R^4$ is $(C_{2-12})$alkenyl.

In one subclass of this class, each $R^4$ is —C(O)$R^5$. In one sub-subclass of this subclass, each $R^5$ is $(C_{1-12})$alkyl unsubstituted or substituted by $R^6$. In one sub-subclass of this subclass, each $R^5$ is $(C_{2-12})$alkenyl unsubstituted or substituted by $R^6$. In one sub-sub-subclass of this sub-subclass, each $R^5$ is $(C_{3-8})$cycloalkyl. In one sub-sub-subclass of this sub-subclass, each $R^5$ is 5- to 9-membered aryl.

In one embodiment, A is cyclooctyl. In one class of this embodiment, each n is an integer from 1 to 3. In one subclass of this class, each $R^4$ is hydrogen. In one subclass of this class, each $R^4$ is $(C_{1-12})$alkyl. In one sub-subclass of this subclass, each $R^4$ is independently ethyl. In one subclass of this class, each $R^4$ is $(C_{2-12})$alkenyl.

In one subclass of this class, each $R^4$ is —C(O)$R^5$. In one sub-subclass of this subclass, each $R^5$ is $(C_{1-12})$alkyl unsubstituted or substituted by $R^6$. In one sub-subclass of this subclass, each $R^5$ is $(C_{e-12})$alkenyl unsubstituted or substituted by $R^6$. In one sub-sub-subclass of this sub-subclass, each $R^5$ is $(C_{3-8})$cycloalkyl. In one sub-sub-subclass of this sub-subclass, each $R^5$ is 5- to 9-membered aryl.

In one embodiment, each n is an integer from 1 to 2. In one embodiment, each n is an integer from 1 to 3. In one embodiment, each n is an integer from 1 to 4. In one embodiment, each n is an integer from 1 to 5. In one embodiment, each n is an integer from 1 to 6. In one embodiment, each n is an integer from 1 to 7. In one embodiment, each n is an integer from 1 to 8. In one embodiment, each n is an integer from 1 to 9. In one embodiment, each n is an integer from 1 to 10. In one embodiment, each n is 1. In one embodiment, each n is 2. In one embodiment, each n is 3. In one embodiment, each n is 4. In one embodiment, each n is 5. In one embodiment, each n is 6. In one embodiment, each n is 7. In one embodiment, each n is 7. In one embodiment, each n is 8. In one embodiment, each n is 9. In one embodiment, each n is 10. In one embodiment, each n is 11. In one embodiment, each n is 12. In one embodiment, each n is 13. In one embodiment, each n is 14. In one embodiment, each n is 15.

In one embodiment, the compound of formula III has a volatile organic content of less than 50 wt % according to ASTM D6886. In one class of this embodiment, the volatile organic content is less than 30 wt %. In one class of this embodiment, the volatile organic content is less than 10 wt %. In one class of this embodiment, the volatile organic content is less than 5 wt %. In one class of this embodiment, the volatile organic content is less than 3 wt %. In one class of this embodiment, the volatile organic content is less than 2 wt %. In one class of this embodiment, the volatile organic content is less than 1 wt %. In one class of this embodiment, the volatile organic content is less than 0.8 wt %.

The present application also discloses a compound according to Formula III:

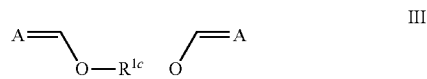

III wherein: each A is independently (a)

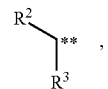

wherein ** indicates the point of attachment, or (b) $(C_{3-8})$cycloalkyl; $R^{1c}$ is each

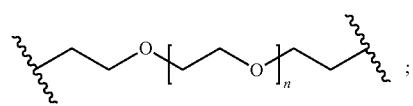

$R^2$ is independently $(C_{2-12})$alkyl; each $R^3$ is independently $(C_{1-12})$alkyl; and n is an integer from 1 to 15.

In one embodiment, each A is

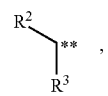

wherein ** indicates the point of attachment. In one class of this embodiment, n is an integer 1 to 3.

In one class of this embodiment, $R^2$ is ethyl, propyl, butyl, pentyl, heptyl, hexyl, heptyl, octyl, nonyl, or decyl. In one subclass of this class, $R^3$ is methyl, ethyl, propyl, butyl, pentyl, heptyl, hexyl, heptyl, octyl, nonyl, or decyl. In one sub-subclass of this subclass, n is an integer from 1 to 3.

In one class of this embodiment, $R^2$ is ethyl, propyl, butyl, or pentyl; and $R^3$ is methyl, ethyl, or propyl. In one subclass of this class, n is an integer from 1 to 3.

In one class of this embodiment, $R^2$ is butyl; and $R^3$ is ethyl. In one subclass of this class, n is an integer from 1 to 3.

In one embodiment, each A is $(C_{3-8})$cycloalkyl. In one class of this embodiment, n is an integer from 1 to 3.

In one class of this embodiment, A is cyclobutyl, cyclopentyl, cyclohexyl, cycloheptyl, or cyclooctyl. In one subclass of this class, n is an integer from 1 to 3.

In one class of this embodiment, A is cyclohexyl. In one subclass of this class, n is an integer from 1 to 3.

In one embodiment, n is an integer from 1 to 2. In one embodiment, n is an integer from 1 to 3. In one embodiment, n is an integer from 1 to 4. In one embodiment, n is an integer from 1 to 5. In one embodiment, n is an integer from 1 to 6. In one embodiment, n is an integer from 1 to 7. In one embodiment, n is an integer from 1 to 8. In one embodiment, n is an integer from 1 to 9. In one embodiment, n is an integer from 1 to 10. In one embodiment, n is 1. In one embodiment, n is 2. In one embodiment, n is 3. In one embodiment, n is 4. In one embodiment, n is 5. In one embodiment, n is 6. In one embodiment, n is 7. In one embodiment, n is 7. In one embodiment, n is 8. In one embodiment, n is 9. In one embodiment, n is 10. In one embodiment, n is 11. In one embodiment, n is 12. In one embodiment, n is 13. In one embodiment, n is 14. In one embodiment, n is 15.

In one embodiment, the compound of formula III has a volatile organic content of less than 50 wt % according to ASTM D6886. In one class of this embodiment, the volatile organic content is less than 30 wt %. In one class of this embodiment, the volatile organic content is less than 10 wt %. In one class of this embodiment, the volatile organic content is less than 5 wt %. In one class of this embodiment, the volatile organic content is less than 3 wt %. In one class of this embodiment, the volatile organic content is less than 2 wt %. In one class of this embodiment, the volatile organic content is less than 1 wt %. In one class of this embodiment, the volatile organic content is less than 0.8 wt %.

Compositions

The compounds disclosed in the present application exhibit a low volatile organic content (less than 50 wt %, but as low as 0.7 wt % according to ASTM D6886), and formulate and have coalescing properties similarly or better than coalescing aids such as 2,24-trimethylpentane-1,3-diol monoisobutyrate. Therefore, the compounds disclosed in the present application are desirable in coating compositions.

The present application discloses a composition comprising the compound of Formula I, II, or III. In one embodiment, the composition comprises the compound Formula I. In one embodiment, the composition comprises the compound Formula II. In one embodiment, the composition comprises the compound Formula III.

The present application discloses a composition comprising the compound of Formula I, II or III; and a polymer. In one class of this embodiment, the polymer is a latex polymer. In one subclass of this class, the latex polymer has a $T_g$ in the range of from about −20° C. to about 100° C. In one subclass of this class, the latex polymer has a $T_g$ in the range of from about 2° C. to about 60° C.

In one subclass of this class, the latex polymer is chosen from an acrylic, a vinyl acrylic, a styrene butadiene or a styrene acrylic latex polymer. In one sub-subclass of this subclass, the latex polymer is an acrylic latex polymer. In one sub-subclass of this subclass, the latex polymer is a vinyl latex polymer. In one sub-subclass of this subclass, the latex polymer is styrene butadiene latex polymer. In one sub-subclass of this subclass, the latex polymer is a styrene acrylic latex polymer.

In one class of this embodiment, the compound of Formula I, II or III is present from about 1 to about 20 phr relative to the sum total of the polymer. In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 5° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 2° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one class of this embodiment, the compound of Formula I, II or III is present from about 1 to about 15 phr relative to the sum total of the polymer. In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 5° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 2° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one class of this embodiment, the compound of Formula I, II or III is present from about 1 to about 10 phr relative to the sum total of the polymer. In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 5° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 2° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one class of this embodiment, the compound of Formula I, II or III is present from about 1 to about 8 phr relative to the sum total of the polymer. In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 5° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 2° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one class of this embodiment, the compound of Formula I, II or III is present from about 1 to about 6 phr relative to the sum total of the polymer. In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 5° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 2° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one class of this embodiment, the compound of Formula I, II or III is present from about 1 to about 5 phr relative to the sum total of the polymer. In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 5° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 2° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one class of this embodiment, the compound of Formula I, II or III is present from about 1 to about 4 phr relative to the sum total of the polymer. In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 5° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 60° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one subclass of this class, the composition has a minimum film formation temperature in the range of from about −35° C. to about 2° C. In one sub-subclass of this sub class, the polymer is a latex polymer. In one sub-sub-subclass of this sub-subclass, the latex polymer has a $T_g$ in the range of from about −20° C. to about 100° C. In one sub-sub-subclass of this sub-subclass, the latex polymer has a $T_g$ in the range of from about 2° C. to about 60° C. In one sub-sub-subclass of this sub-subclass, the latex polymer is chosen from an acrylic, a vinyl acrylic, a styrene butadiene or a styrene acrylic latex polymer.

In one embodiment, the compound of Formula I, II, or III has a volatile organic content of less than 50 wt % according to ASTM D6886. In one embodiment, the compound of Formula I, II, or III has a volatile organic content of less than 40 wt % according to ASTM D6886. In one embodiment, the compound of Formula I, II, or III has a volatile organic content of less than 30 wt % according to ASTM D6886. In one embodiment, the compound of Formula I, II, or III has a volatile organic content of less than 20 wt % according to ASTM D6886. In one embodiment, the compound of Formula I, II, or III has a volatile organic content of less than 10 wt % according to ASTM D6886. In one embodiment, the compound of Formula I, II, or III has a volatile organic content of less than 5 wt % according to ASTM D6886.

In one embodiment, the compound of Formula I, II, or III is chosen from

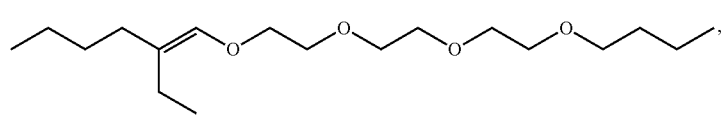

1

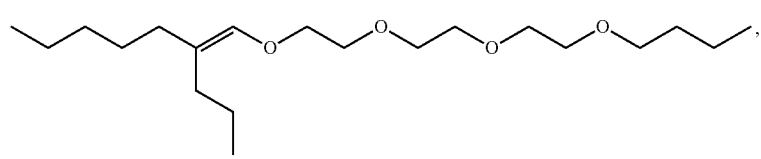

2

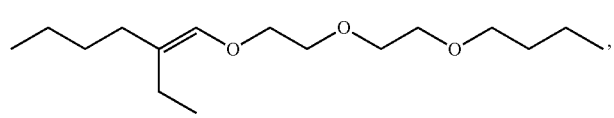

3

-continued
4
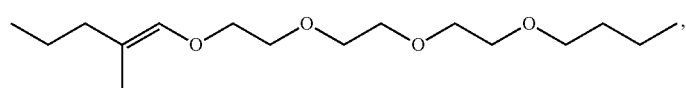
6
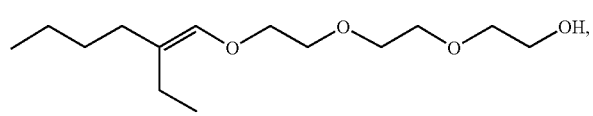
7
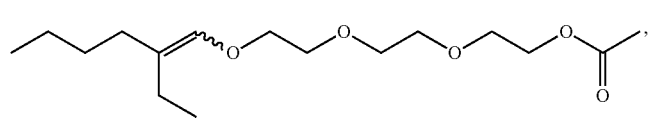
8
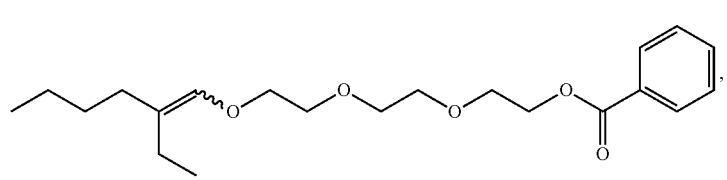
10
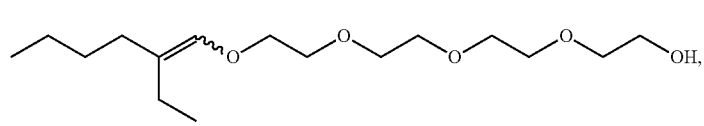
11 12
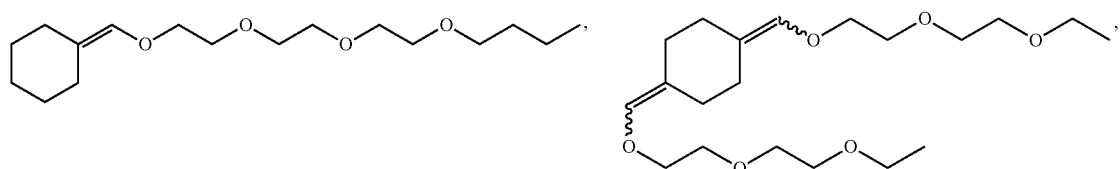
13
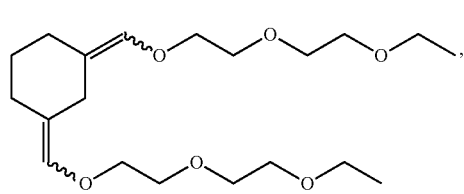
5
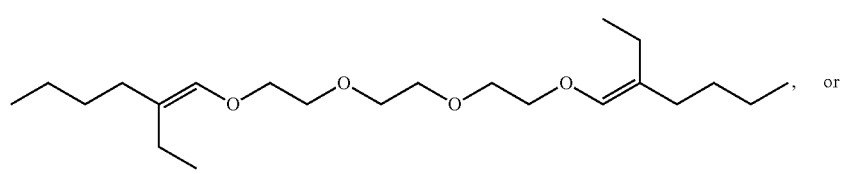, or
9
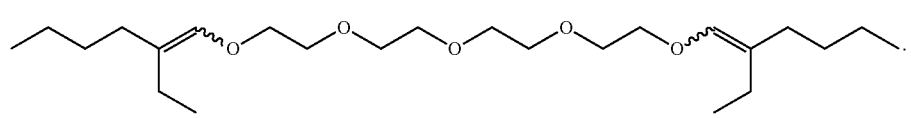.
In one class of this embodiment, the compound is the compound of Formula I, which is chosen from
1
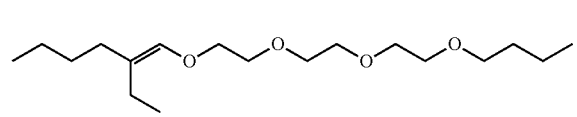
2
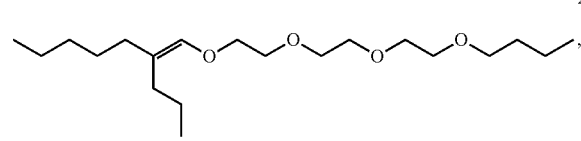
-continued
3
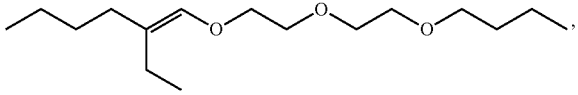
4
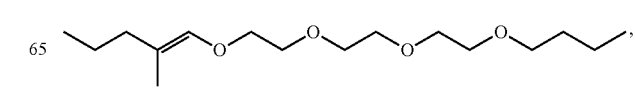

6
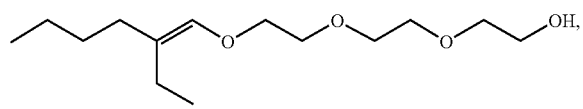

7
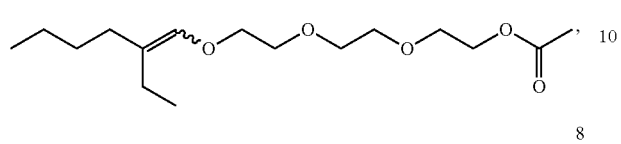

8
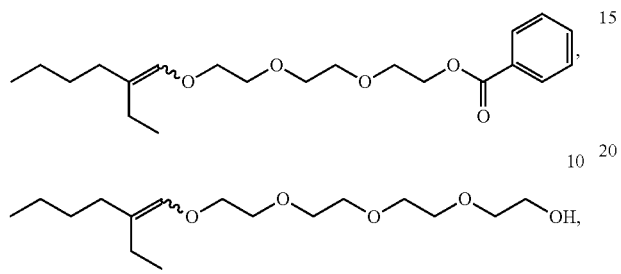

10
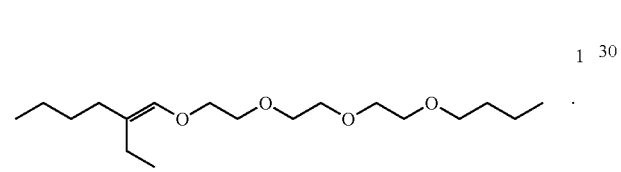

In one subclass of this class, the compound is the compound of Formula I, which is 1
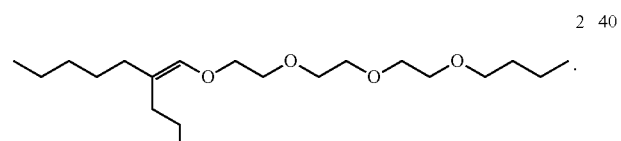

In one subclass of this class, the compound is the compound of Formula I, which is 2
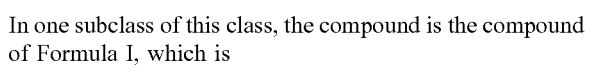

In one subclass of this class, the compound is the compound of Formula I, which is 3
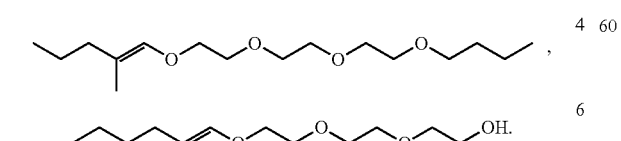

In one subclass of this class, the compound is the compound of Formula I, which is 4
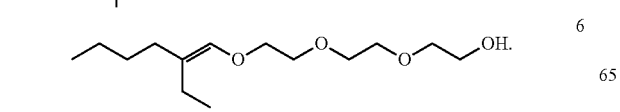

6
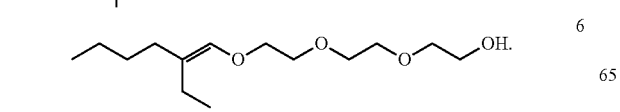

In one subclass of this class, the compound is the compound of Formula I, which is 7
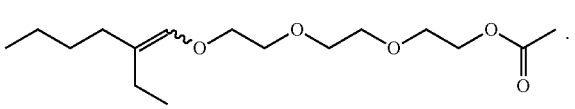

In one subclass of this class, the compound is the compound of Formula I, which is 8
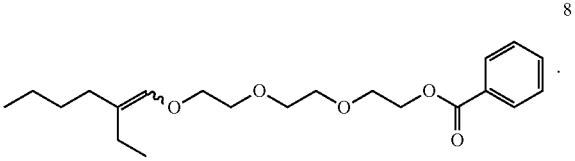 [SMILES: CCCCC(=COCCOCCOCCOC(=O)c1ccccc1)CC]

In one subclass of this class, the compound is the compound of Formula I, which is 10
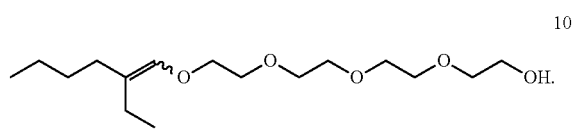 [SMILES: CCCCC(=COCCOCCOCCOCCO)CC]

In one subclass of this class, the compound is the compound of Formula I, which is 11
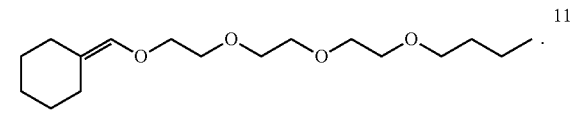 [SMILES: CCCCOCCOCCOCCOC=C1CCCCC1]

In one class of this embodiment, the compound is the compound of Formula II, which is chosen from 12
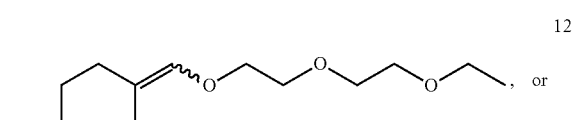, or 13
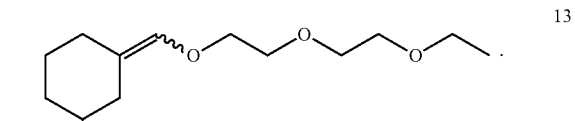

In one subclass of this class, the compound is the compound of Formula II, which is

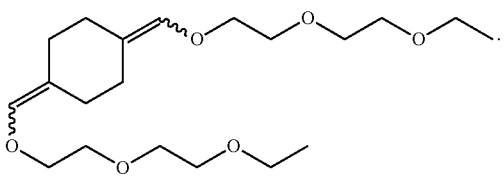

In one subclass of this class, the compound is the compound of Formula II, which is

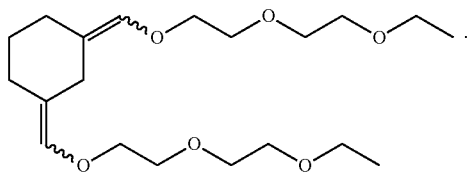

In one class of this embodiment, the compound is the compound of Formula III, which is chosen from

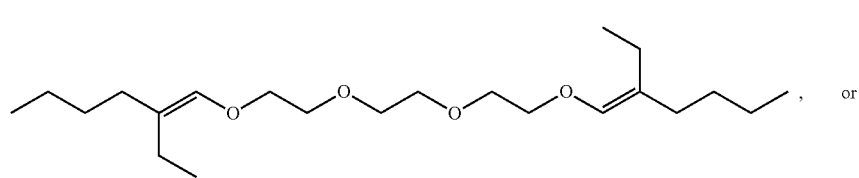, or

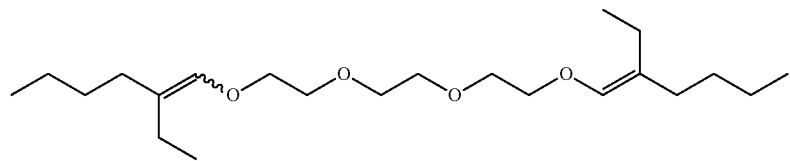

In one subclass of this class, the compound is the compound of Formula III, which is

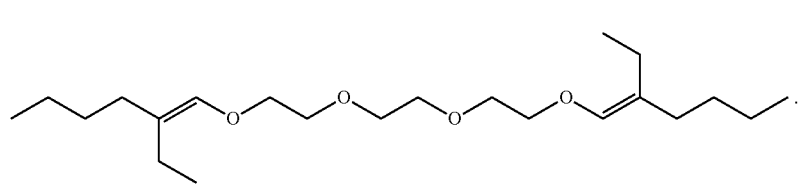

In one subclass of this class, the compound is the compound of Formula III, which is

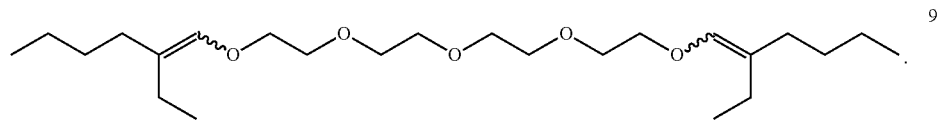 [SMILES: CCCCC(=COCCOCCOCCOCCOC=C(CC)CCCC)CC]

The compounds (i.e., Formula I, II, or III) of the present invention useful as reactive coalescents according to the invention include those having a weight percent volatile content of less than 50%, as measured according to ASTM Method D6886. This test may be conducted generally by heating the sample in a forced air oven at 110° C. for 60 minutes. The weight loss after the test is deemed to result from a loss of volatiles originally present in the sample; the percent volatile present in the original sample may then be calculated. Although the cited test can be conducted on coating compositions containing other components such as latex polymers, the values cited herein may be obtained from a sample of the coalescent itself. The weight percent volatile of a coalescent may be used herein as a yardstick to measure the amount of VOC the coalescent would contribute to the VOC of a coating composition.

Examples of the "latex polymers" useful according to the invention include aqueous vinyl polymers, which are the reaction products of one or more ethylenically unsaturated monomers. Examples of the ethylenically unsaturated monomers include, but are not limited to, styrene, methyl acrylate, methyl methacrylate, ethyl acrylate, ethyl methacrylate, butyl acrylate, butyl methacrylate, isobutyl acrylate, isobutyl methacrylate, ethylhexyl acrylate, 2-ethylhexyl methacrylate, 2-ethylhexyl acrylate, isoprene, octyl acrylate, octyl methacrylate, iso-octyl acrylate, iso-octyl methacrylate, acrylic acid, methacrylic acid, itaconic acid, crotonic acid, O-methyl styrene, vinyl naphthalene, vinyl toluene, chloromethyl styrene, hydroxyethyl (meth)acrylate, hydroxypropyl (meth)acrylate, acrylonitrile, glycidyl methacrylate, acetoacetoxyethyl methacrylate, acetoacetoxy ethyl acrylate, vinyl chloride, vinylidene chloride, vinyl acetate, butyl acrylamide, ethyl acrylamide, 2-hydroxyethyl methacrylate phosphate and the like.

Latex emulsion polymers are well known in the art of coating compositions, and we do not intend the term to be especially limiting, although some latex emulsion polymers may be better suited as coating compositions, either inherently or in combination with the coalescents of the invention. Examples of commercial latex emulsion polymers useful according to the invention include Rhoplex™ SG-30, Rhoplex™ HG-74P, Rhoplex™ SG-10M, Rhoplex™ AC2508, Ucar™ 626, and Ucar™ 379G (all available from The Dow Chemical Company), Acronal™ 296D (BASF Corp.), Aquamac™ 705 and Aquamac™ 588 (Hexion Specialty Chemicals), and the like.

In one embodiment, the polymer is a latex polymer, and the latex polymers useful according to the invention may be a homopolymer, or a copolymer of an ethylenically unsaturated monomer and one or more additional copolymerizable monomers.

The latex emulsion polymers useful according to the invention are addition polymers that may be formed via a free radical addition polymerization. In such addition polymers, the propagating species may be a free radical, and the polymer is formed in a chain-growth fashion polymerization as understood in the art. As noted, these polymers are latex emulsion polymers in which a monomer solution may be emulsified in an aqueous solution, and under agitation reacted via a free-radical polymerization process as described herein, to form latex particles.

The water-based latexes useful according to the invention may generally be prepared by polymerizing acrylic (ethylenically unsaturated) monomers. Before conducting polymerization, these ethylenically unsaturated monomers are either pre-emulsified in water/surfactant mixture or used as such.

The polymerization process of making these 'acrylic' latexes may also require an initiator (oxidant), a reducing agent, or a catalyst. Suitable initiators include conventional initiators such as ammonium persulfate, sodium persulfate, hydrogen peroxide, t-butyl hydroperoxide, ammonium or alkali sulfate, di-benzoyl peroxide, lauryl peroxide, di-tertiarybutylperoxide, 2,2-azobisisobutyronitrile, benzoyl peroxide, and the like.

Suitable reducing agents are those which increase the rate of polymerization and include, for example, sodium bisulfite, sodium hydrosulfite, sodium formaldehyde sulfoxylate, ascorbic acid, isoascorbic acid, and mixtures thereof.

Suitable catalysts are those compounds which promote decomposition of the polymerization initiator under the polymerization reaction conditions thereby increasing the rate of polymerization. Suitable catalysts include transition metal compounds and driers. Examples of such catalysts include, but are not limited to ferrous sulfate heptahydrate, ferrous chloride, cupric sulfate, cupric chloride, cobalt acetate, cobaltous sulfate, and mixtures thereof.

The latex polymers of the invention are prepared from monomers characterized as being ethylenically unsaturated monomers that can participate in addition polymerization reactions. As used herein, ethylenically unsaturated monomers may also be described as vinyl monomers. The polymers made from such monomers are addition polymers, and may be formed as emulsion polymers, also known as latexes or latex emulsions.

The latex polymers useful according to the invention may have pendant moieties, meaning that the ethylenically unsaturated monomers used to prepare the latex polymers of the invention have been reacted into an addition polymer, and that a portion of the monomers remains as a pendant moiety. Alternatively, we may say that the polymers according to the invention have residues from the ethylenically unsaturated monomers of the invention, in which case we mean that the monomers have been reacted into an addition polymer via their ethylenic unsaturation, and that a portion of the monomers remains as a residue. Both these descriptions are well-known in the art of addition polymers, and the descriptions are not otherwise intended to be especially limiting.

The invention relates to the use of emulsion polymers which are also known as latexes, or as used herein, latex emulsions. In these latexes, the polymers formed may have a particle size ranging, for example, from about 80 nm to about 300 nm, or from 100 nm to 250 nm, or from 125 nm to 200 nm. The Te of such latexes may range, for example, from about 0° C. to about 80° C., or from 15° C. to 60° C., or from 20° C. to 40° C.

The latex polymers useful according to the invention may be prepared by an emulsion free-radical polymerization of ethylenically unsaturated monomers. These latex polymers may be homopolymers, or may be copolymers formed from more than one ethylenically unsaturated monomer.

Examples of ethylenically unsaturated monomers include, but are not limited to, acrylic and methacrylic acid esters such as methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, isooctyl (meth)acrylate, isodecyl (meth)acrylate, lauryl (meth)acrylate, stearyl (meth)acrylate, phenoxyethyl (meth)acrylate, methoxyethyl (meth)acrylate, benzyl (meth)acrylate, ethoxyethyl (meth)acrylate, 2-ethylhexyl (meth)acrylate, cyclopentyl (meth)acrylate and isobutyl (meth)acrylate, as well as combinations of these monomers. A combination of these monomers may be used in order to achieve an appropriate $T_g$ or other properties for the latex emulsion polymer.

Such acrylic and methacrylic acid esters having a C1-C20alcohol moiety are commercially available or can be prepared by known esterification processes. The acrylic and methacrylic acid ester may contain additional functional groups, such as, hydroxyl, amine, halogen, ether, carboxylic acid, amide, nitrile, and alkyl group. Such esters include carbodiimide (meth)acrylate, methyl (meth)acrylate, ethyl (meth)acrylate, butyl (meth)acrylate, isobutyl (meth)acrylate, ethylhexyl (meth)acrylate, octyl (meth)acrylate, isobutyl (meth)acrylate, allyl (meth)acrylate, and glycidyl (meth)acrylate.

Additional suitable polymerizable ethylenically unsaturated monomers include styrenic monomers. Styrenic monomers include styrene, as well as substituted styrenes such as C1-C6 alkyl ring-substituted styrene, C1-C3 alkyl alpha-substituted styrene or a combination of ring and an alpha-alkyl substituted styrene. Such styrenic polymerizable monomers include styrene, p-methyl styrene, o-methyl styrene, p-butyl styrene, alpha-methyl styrene, and combinations thereof.

In addition, vinyl esters may be used as copolymerizable mono-ethylenically unsaturated monomers, including vinyl esters of vinyl alcohol such as the VEOVA series available from Shell Chemical Company as VEOVA 5, VEOVA 9, VEOVA 10, and VEOVA 11 products. See O. W. Smith, M. J. Collins, P. S. Martin, and D. R. Bassett, Prog. Org. Coatings 22, 19 (1993).

In general, the vinyl monomers may be polymerized by a conventional emulsion free-radical initiated polymerization technique. The polymerization can be initiated by a water soluble or water-dispersible free-radical initiator, optionally in combination with a reducing agent, at an appropriate temperature, for example from 55 to 90° C. The polymerization of the monomers may be conducted batch wise, semi-batch, or in a continuous mode.

A conventional surfactant or a combination of surfactants may be used such as anionic or non-ionic emulsifier in the suspension or emulsion polymerization to prepare a polymer of the invention. Examples of such surfactants include, but are not limited to, alkali or ammonium alkylsulfate, alkylsulfonic acid, or fatty acid, oxyethylated alkylphenol, or any combination of anionic or non-ionic surfactant. A surfactant monomer may be used such as HITENOL HS-20 (which is a polyoxyethylene alkylphenyl ether ammonium sulfate available from DKS International, Inc., Japan). A list of surfactants is available in the treatise: McCutcheon's Emulsifiers & Detergents, North American Edition and International Edition, MC Publishing Co., Glen Rock, N.J. 1993. The amount of the surfactant used is usually between 0.1 to 6 wt %, based on the total weight of the monomers.

As polymerization initiators, any conventional free-radical initiator may be used such as hydrogen peroxide, t-butyl-hydroperoxide, ammonium or alkali sulfate, di-benzoyl peroxide, lauryl peroxide, di-tertiarybutylperoxide, 2,2'-azobisisobutyronitrile, benzoyl peroxide, and the like. The amount of the initiator is typically between 0.05 to 6.0 wt %, based on the total weight of the total monomers. A free-radical initiator may be combined with a reducing agent to form a redox initiating system. Suitable reducing agents are those which increase the rate of polymerization and include, for example, sodium bisulfite, sodium hydrosulfide, sodium, ascorbic acid, isoascorbic acid and mixtures thereof. The redox initiating system can be used at similar levels as the free-radical initiators.

In addition, in combination with the initiators and reducing agents, polymerization catalysts may be used. Polymerization catalysts are those compounds which increase the rate of polymerization by promoting decomposition of the free radical initiator in combination with the reducing agent at the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

In addition, a low level of a chain transfer agent may also be used to prepare a latex polymer useful in accordance with the invention. Suitable chain transfer agents include, but are not limited to, butyl mercaptan, n-octylmercaptan, n-dodecyl mercaptan, butyl or methyl mercaptopropionate, mercaptopropionic acid, 2-ethylhexyl 3-mercaptopropionate, n-butyl 3-mercaptopropionate, isodecylmercaptan, octadecylmercaptan, mercaptoacetic acid, haloalkyl compounds, (such as carbon tetrabromide and bromodichoromethane), and the reactive chain transfer agents described in U.S. Pat. No. 5,247,040, incorporated herein by reference. In particular, mercaptopropionate, allyl mercaptopropionate, allyl mercaptoacetate, crotyl mercaptopropionate and crotyl mercaptoacetate, and mixtures thereof, represent preferred chain transfer agents.

A copolymerizable monomer known to promote wet adhesion may also be incorporated into the polymer. Examples of wet adhesion promoting monomers include, but are not limited to, nitrogen-containing monomers such as t-butylaminoethyl methacrylate, dimethylaminoethyl methacrylate, diethylaminoethyl methacrylate, N,N-dimethylaminopropylmethacrylamide, 2-t-butylaminoethyl methacrylate, N,N dimethylaminoethyl acrylate and N-(2-methacryloyloxy ethyl)ethylene urea.

Water-dispersible and water-soluble polymers may also be employed as surfactants or stabilizers in accordance with the present invention. Examples of such polymeric stabilizers include water-dispersible polyesters as described in U.S. Pat. Nos. 4,946,932 and 4,939,233; water-dispersible polyurethanes as described in U.S. Pat. Nos. 4,927,876 and 5,137,961; and alkali-soluble acrylic resins as described in U.S. Pat. No. 4,839,413, all of which are incorporated herein by reference. Cellulosics and polyvinyl alcohols may also be used.

Surfactants and stabilizers may be used during the polymerization to control, for example, particle nucleation and growth, particle size and stability or they may be post-added to enhance stability of the latex or to modify other properties of the latex such as surface tension, wettability, and the like.

At least one ethylenically unsaturated copolymerizable surfactant may be employed, for example those possessing isopropenyl phenyl or allyl groups. Copolymerizable surfactants may be anionic, such as containing a sulfate or sulfonate group, or nonionic surfactants. Other copolymerizable surfactants include those containing polyoxyethylene alkyl phenyl ether moieties. Additional copolymerizable surfactants include sodium alkyl allyl sulfosuccinate.

The latex polymers in accordance with the invention may have a weight average molecular weight (Mw), for example, of from 1,000 to 1,000,000, as determined by gel permeation chromatography (GPC), or from 5,000 to 250,000.

The particle size for the aqueous dispersions in accordance with the invention may be, for example, from about 0.01 to about 25 μm, or from 0.05 to 1 μm, or from 0.075 to 500 μm. In an emulsion polymerization in accordance with the invention, the particle size of the latex may range, for example, from 0.01 to 5 μm.

The latex particles generally have a spherical shape, and the spherical polymeric particles may have a core portion and a shell portion or a gradient structure. The core/shell polymer particles may also be prepared in a multi-lobe form, a peanut shell, an acorn form, a raspberry form, or any other form. If the particles have a core/shell structure, the core portion may comprise from about 20 to about 80 wt % of the total weight of the particle, and the shell portion may comprise about 80 to about 20 wt % of the total weight of the particle.

The glass transition temperature (Tg) of the latex polymers in accordance with the present invention, in the absence of the coalescents described herein, may be up to about 100° C. In a preferred embodiment of the present invention, where a film forming at ambient temperatures of the particles is desirable, the glass transition temperature of the polymer itself may preferably be under 60° C.

The latex polymers of the invention may comprise enamine functional polymers, with the enamine functionality serving to improve the hydrolytic stability of the acetoacetoxy group. Enamine functional polymers have been described in Polymer Bulletin 32, 419-426 (1994). Additionally, enamine functional polymers are described in European Patent Application No. 0492847 A2; U.S. Pat. Nos. 5,296,530; and 5,484,849.

The coating compositions of the invention may further comprise other components commonly used in paint formulations, such as, for example, pigments, filler, rheology modifiers, thickeners, wetting and dispersing agents, deformers, freeze-thaw additives, colorants, open-time additives, driers, catalysts, crosslinkers, biocides, light stabilizers, and the like.

The driers are capable of promoting oxidative crosslinking of the unsaturated moieties and providing enhanced coating properties. Examples of commercial driers include Zirconium Hex-Cem®, Cobalt Ten-Cem®, calcium Cem-All®, Zirconium Hydro-Cem, and Cobalt Hydro-Cure® II sold by OMG Americas of West-Lake, Ohio. Examples of driers based on unsaturated fatty alcohols include oleyl alcohol, linoleoyl alcohol, geraniol, or citronellol.

In one embodiment, the composition has a minimum film formation temperature in the range of from about −35° C. to about 60° C. In one embodiment, the composition has a minimum film formation temperature in the range of from about −35° C. to about 5° C. In one embodiment, the composition has a minimum film formation temperature in the range of from about −35° C. to about 60° C. In one embodiment, the composition has a minimum film formation temperature in the range of from about −35° C. to about 2° C.

The minimum film formation temperature of a latex is the lowest temperature at which the latex forms a practical film. MFFT can be measured using ASTM D2354. The efficiency of a coalescent can be determined by determining the amount of the coalescent required to reduce the MFFT of a latex polymer to 4.4° C., which is the lowest desirable application temperature of a paint. It is generally considered unacceptable if the amount of the coalescent present in a paint formulation exceeds 20% by weight based on the solids of the latex polymer. This is particularly important for a non-volatile coalescent since the coalescent will remain in the dried film and cause a detrimental effect on the coating properties such as, for example, hardness, scrub resistance, and block resistance. As shown in the Table 2, the level of coalescent in phr required to lower the MFFT of a variety of latex resins is less than 7 phr at 4.4° C. and less than 8.5 phr at 1.67° C., exemplifying the coalescent efficiency of these materials.

Processes

The present application also discloses a one-pot process for preparing an enol ether which comprises: (1) reacting: (i) an acetal; or (ii) an alcohol, and an aldehyde; in the presence of a catalyst of Formula IV:

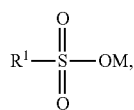

I wherein: $R^1$ is (1) $(C_{1-20})$alkyl, (2) $(C_{3-8})$cycloalkyl, or (3) a 6- to 9-membered aryl, unsubstituted or substituted by 1- to 5 $(C_{1-20})$alkyl substituents; M is an alkaline metal cation, wherein the reaction is carried out at a temperature range of from about 50° C. to about 300° C.

The alcohol can contain one or more alcohol groups. For example, the alcohol can be a mono-ol, a diol or trial. The aldehyde can contain one or more aldehyde groups. For example, the aldehyde can be a mono-al, a di-al or a trial. The acetal can be made from one alcohol or a mixture of alcohols. Therefore, the acetal can be a pure or mixed acetal.

In one embodiment, the yield of the enol ether is greater than 50%, based on the acetal or the aldehyde. In one class of this embodiment, the enol ether has a Gardner color of less than 2 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one class of this embodiment, the enol ether has a Gardner color of less than 1 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one embodiment, the yield of the enol ether is greater than 60%, based on the acetal or the aldehyde. In one class of this embodiment, the enol ether has a Gardner color of less than 2 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV. In one class of this embodiment, the enol ether has a Gardner color of less than 1 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one embodiment, the yield of the enol ether is greater than 70%, based on the acetal or the aldehyde. In one class of this embodiment, the enol ether has a Gardner color of less than 2 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one class of this embodiment, the enol ether has a Gardner color of less than 1 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one embodiment, the yield of the enol ether is greater than 80%, based on the acetal or the aldehyde. In one class of this embodiment, the enol ether has a Gardner color of less than 2 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one class of this embodiment, the enol ether has a Gardner color of less than 1 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one embodiment, the yield of the enol ether is greater than 90%, based on the acetal or the aldehyde. In one class of this embodiment, the enol ether has a Gardner color of less than 2 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one class of this embodiment, the enol ether has a Gardner color of less than 1 as measured according to ASTM D 1544. In one subclass of this class, step (1) further comprises 0.01 to about 50 mol % of an acid, based on 100 mol % of the catalyst of Formula IV. In one subclass of this class, step (1) further comprises 0.01 to about 10 mol % of an acid, based on 100 mol % of the catalyst of Formula IV. In one subclass of this class, step (1) further comprises 0.01 to about 0.1 mol % of an acid, based on 100 mol % of the catalyst of Formula IV.

In one embodiment, the catalyst of Formula IV is present from about 0.01 mol % to about 20 mol %, based on 100 mol % of the aldehyde or the acetal. In one embodiment, the catalyst of Formula IV is present from about 0.01 mol % to about 15 mol %, based on 100 mol % of the aldehyde or the acetal. In one embodiment, the catalyst of Formula IV is present from about 0.01 mol % to about 10 mol %, based on 100 mol % of the aldehyde or the acetal. In one embodiment, the catalyst of Formula IV is present from about 0.01 mol % to about 5 mol %, based on 100 mol % of the aldehyde or the acetal. In one embodiment, the catalyst of Formula IV is present from about 0.01 mol % to about 3 mol %, based on 100 mol % of the aldehyde or the acetal. In one embodiment, the catalyst of Formula IV is present from about 0.01 mol % to about 2 mol %, based on 100 mol % of the aldehyde or the acetal. In one embodiment, the catalyst of Formula IV is present from about 0.01 mol % to about 1 mol %, based on 100 mol % of the aldehyde or the acetal.

In one embodiment, step (1) further comprises 0.01 to about 50 mol % of an acid, based on 100 mol % of the catalyst of Formula IV. In one class of this embodiment, the acid is the conjugate acid of the catalyst of Formula IV. In one embodiment, step (1) further comprises 0.01 to about 20 mol % of an acid, based on 100 mol % of the catalyst of Formula IV. In one class of this embodiment, the acid is the conjugate acid of the catalyst of Formula IV. In one embodiment, step (1) further comprises 0.01 to about 10 mol % of an acid, based on 100 mol % of the catalyst of Formula IV.

In one class of this embodiment, the acid is the conjugate acid of the catalyst of Formula IV. In one embodiment, step (1) further comprises 0.01 to about 5 mol % of an acid, based on 100 mol % of the catalyst of Formula IV. In one class of this embodiment, the acid is the conjugate acid of the catalyst of Formula IV. In one embodiment, step (1) further comprises 0.01 to about 3 mol % of an acid, based on 100 mol % of the catalyst of Formula IV. In one class of this embodiment, the acid is the conjugate acid of the catalyst of Formula IV. In one embodiment, step (1) further comprises 0.01 to about 2 mol % of an acid, based on 100 mol % of the catalyst of Formula IV. In one class of this embodiment, the acid is the conjugate acid of the catalyst of Formula IV. In one embodiment, step (1) further comprises 0.01 to about 1 mol % of an acid, based on 100 mol % of the catalyst of Formula IV. In one class of this embodiment, the acid is the conjugate acid of the catalyst of Formula IV. In one embodiment, step (1) further comprises 0.01 to about 0.5 mol % of an acid, based on 100 mol % of the catalyst of Formula IV. In one class of this embodiment, the acid is the conjugate acid of the catalyst of Formula IV. In one embodiment, step (1) further comprises 0.01 to about 0.3 mol % of an acid, based on 100 mol % of the catalyst of Formula IV. In one class of this embodiment, the acid is the conjugate acid of the catalyst of Formula IV. In one embodiment, step (1) further comprises 0.01 to about 0.1 mol % of an acid, based on 100 mol % of the catalyst of Formula IV. In one class of this embodiment, the acid is the conjugate acid of the catalyst of Formula IV.

The acid can be any chemical capable of donating a proton or a chemical capable of forming a covalent bond with an electron pair. Nonlimiting examples include p-toluene sulfonic acid, methane sulfonic acid, trifluoromethane sulfonic acid, benzene sulfonic acid, ethane sulfonic acid, hydrogen chloride, sulfuric acid, trifluoroacetic acid, acetic acid, oxalic acid, citric acid, fatty acids (e.g., lauric acid, palmoatic acid, and the like), polymeric acids such as polystyrene sulfonate, sodium bicarbonate, sodium bisulfate, ascorbic acid, and the like.

In one embodiment, the acid is the conjugate acid of the catalyst of Formula IV. In one class of this embodiment, the acid is p-toluene sulfonic acid or methane sulfonic acid.

In one embodiment, the alcohol in step (1) is present at least 100 mol %, based on 100 mol % of the aldehyde. In one embodiment, the alcohol in step (1) is present in the range of from about 100 mol % to about 400 mol %, based on 100 mol % of the aldehyde. In one embodiment, the alcohol in step (1) is present in the range of from about 100 mol % to about 300 mol %, based on 100 mol % of the aldehyde. In one embodiment, the alcohol in step (1) is present in the range of from about 100 mol % to about 200 mol %, based on 100 mol % of the aldehyde.

In one embodiment, the process is carried out by reactive distillation conditions.

In one embodiment, the process further comprises step (2) separating the enol ether.

In one class of this embodiment, the yield of the separated enol ether is greater than 50%, based on the acetal or the aldehyde. In one class of this embodiment, the yield of the separated enol ether is greater than 60%, based on the acetal or the aldehyde. In one class of this embodiment, the yield of the separated enol ether is greater than 70%, based on the acetal or the aldehyde. In one class of this embodiment, the yield of the separated enol ether is greater than 80%, based on the acetal or the aldehyde. In one class of this embodiment, the yield of the separated enol ether is greater than 90%, based on the acetal or the aldehyde.

In one class of this embodiment, the separated enol ether of step (2) has a Gardner color of less than 3 as measured according to ASTM D 1544. In one subclass of this class, the yield of the separated enol ether is greater than 50%, based on the acetal or the aldehyde. In one subclass of this class, the yield of the separated enol ether is greater than 60%, based on the acetal or the aldehyde. In one subclass of this class, the yield of the separated enol ether is greater than 70%, based on the acetal or the aldehyde. In one subclass of this class, the yield of the separated enol ether is greater than 80%, based on the acetal or the aldehyde. In one subclass of this class, the yield of the separated enol ether is greater than 90%, based on the acetal or the aldehyde.

In one class of this embodiment, the separated enol ether of step (2) has a Gardner color of less than 2 as measured according to ASTM D 1544. In one subclass of this class, the yield of the separated enol ether is greater than 50%, based on the acetal or the aldehyde. In one subclass of this class, the yield of the separated enol ether is greater than 60%, based on the acetal or the aldehyde. In one subclass of this class, the yield of the separated enol ether is greater than 70%, based on the acetal or the aldehyde. In one subclass of this class, the yield of the separated enol ether is greater than 80%, based on the acetal or the aldehyde. In one subclass of this class, the yield of the separated enol ether is greater than 90%, based on the acetal or the aldehyde.

In one embodiment, the reaction is carried out at a temperature range of from about 80° C. to about 300° C. In one class of this embodiment, the pressure at which the reaction is carried out is from about 101.3 kPa to about 0.1 kPa. In one class of this embodiment, the pressure at which the reaction is carried out is from about 50 kPa to about 0.1 kPa. In one class of this embodiment, the pressure at which the reaction is carried out is from about 10 kPa to about 0.1 kPa. In one class of this embodiment, the pressure at which the distillation is carried out is from about 3 kPa to about 0.1 kPa. In one class of this embodiment, the pressure at which the distillation is carried out is from about 1 kPa to about 0.1 kPa.

In one embodiment, the reaction of step (1) is carried out at a temperature range of from about 100° C. to about 300° C. In one class of this embodiment, the pressure at which the reaction of step (1) is carried out is from about 101.3 kPa to about 0.1 kPa. In one class of this embodiment, the pressure at which the reaction of step (1) is carried out is from about 50 kPa to about 0.1 kPa. In one class of this embodiment, the pressure at which the reaction of step (1) is carried out is from about 10 kPa to about 0.1 kPa. In one class of this embodiment, the pressure at which the distillation is carried out is from about 3 kPa to about 0.1 kPa. In one class of this embodiment, the pressure at which the distillation is carried out is from about 1 kPa to about 0.1 kPa.

In one embodiment, the reaction of step (1) is carried out at a temperature range of from about 120° C. to about 300° C. In one class of this embodiment, the pressure at which the reaction of step (1) is carried out is from about 101.3 kPa to about 0.1 kPa. In one class of this embodiment, the pressure at which the reaction of step (1) is carried out is from about 50 kPa to about 0.1 kPa. In one class of this embodiment, the pressure at which the reaction of step (1) is carried out is from about 10 kPa to about 0.1 kPa. In one class of this embodiment, the pressure at which the reaction of step (1) is carried out is from about 3 kPa to about 0.1 kPa. In one class of this embodiment, the pressure at which the reaction of step (1) is carried out is from about 1 kPa to about 0.1 kPa.

In one embodiment, the reaction of step (1) is carried out at a temperature range of from about 150° C. to about 300° C. In one class of this embodiment, the pressure at which the reaction of step (1) is carried out is from about 101.3 kPa to about 0.1 kPa. In one class of this embodiment, the pressure at which the reaction of step (1) is carried out is from about 50 kPa to about 0.1 kPa. In one class of this embodiment, the pressure at which the reaction of step (1) is carried out is from about 10 kPa to about 0.1 kPa. In one class of this embodiment, the pressure at which the reaction of step (1) is carried out is from about 3 kPa to about 0.1 kPa. In one class of this embodiment, the pressure at which the reaction of step (1) is carried out is from about 1 kPa to about 0.1 kPa.

In one embodiment, the reaction is carried out at a temperature range of from about 200° C. to about 300° C. In one class of this embodiment, the pressure at which the reaction of step (1) is carried out is from about 101.3 kPa to about 0.1 kPa. In one class of this embodiment, the pressure at which the reaction of step (1) is carried out is from about 50 kPa to about 0.1 kPa. In one class of this embodiment, the pressure at which the reaction of step (1) is carried out is from about 10 kPa to about 0.1 kPa. In one class of this embodiment, the pressure at which the reaction of step (1) is carried out is from about 3 kPa to about 0.1 kPa. In one class of this embodiment, the pressure at which the reaction of step (1) is carried out is from about 1 kPa to about 0.1 kPa.

In one embodiment, the reaction is carried out at a temperature range of from about 110° C. to about 185° C. In one class of this embodiment, the pressure at which the reaction of step (1) is carried out is from about 101.3 kPa to about 0.1 kPa. In one class of this embodiment, the pressure at which the reaction of step (1) is carried out is from about 50 kPa to about 0.1 kPa. In one class of this embodiment, the pressure at which the reaction of step (1) is carried out is from about 10 kPa to about 0.1 kPa. In one class of this embodiment, the pressure at which the reaction of step (1) is carried out is from about 3 kPa to about 0.1 kPa. In one class of this embodiment, the pressure at which the reaction of step (1) is carried out is from about 1 kPa to about 0.1 kPa.

In one embodiment, the pressure at which the reaction of step (1) is carried out is from about 90 kPa to about 0.1 kPa. In one embodiment, the pressure at which the reaction of step (1) is carried out is from about 70 kPa to about 0.1 kPa. In one embodiment, the pressure at which the reaction of step (1) is carried out is from about 50 kPa to about 0.1 kPa. In one embodiment, the pressure at which the reaction of step (1) is carried out is from about 30 kPa to about 0.1 kPa. In one embodiment, the pressure at which the reaction of step (1) is carried out is from about 10 kPa to about 0.1 kPa. In one embodiment, the pressure at which the reaction of step (1) is carried out is from about 5 kPa to about 0.1 kPa. In one embodiment, the pressure at which the reaction of step (1) is carried out is from about 3 kPa to about 0.1 kPa. In one embodiment, the pressure at which the distillation is carried out is from about 2 kPa to about 0.1 kPa. In one embodiment, the pressure at which the reaction of step (1) is carried out is from about 1 kPa to about 0.1 kPa.

In one embodiment, the process further comprises step (2) separating the enol ether.

In one class of this embodiment, the yield of the separated enol ether is greater than 50%, based on the acetal or the aldehyde. In one class of this embodiment, the yield of the separated enol ether is greater than 60%, based on the acetal or the aldehyde. In one class of this embodiment, the yield of the separated enol ether is greater than 70%, based on the acetal or the aldehyde. In one class of this embodiment, the yield of the separated enol ether is greater than 80%, based on the acetal or the aldehyde. In one class of this embodiment, the yield of the separated enol ether is greater than 90%, based on the acetal or the aldehyde.

In one class of this embodiment, the separated enol ether of step (2) has a Gardner color of less than 3 as measured according to ASTM D 1544. In one subclass of this class, the yield of the separated enol ether is greater than 50%, based on the acetal or the aldehyde. In one subclass of this class, the yield of the separated enol ether is greater than 60%, based on the acetal or the aldehyde. In one subclass of this class, the yield of the separated enol ether is greater than 70%, based on the acetal or the aldehyde. In one subclass of this class, the yield of the separated enol ether is greater than 80%, based on the acetal or the aldehyde. In one subclass of this class, the yield of the separated enol ether is greater than 90%, based on the acetal or the aldehyde.

In one class of this embodiment, the separated enol ether of step (2) has a Gardner color of less than 2 as measured according to ASTM D 1544. In one subclass of this class, the yield of the separated enol ether is greater than 50%, based on the acetal or the aldehyde. In one subclass of this class, the yield of the separated enol ether is greater than 60%, based on the acetal or the aldehyde. In one subclass of this class, the yield of the separated enol ether is greater than 70%, based on the acetal or the aldehyde. In one subclass of this class, the yield of the separated enol ether is greater than 80%, based on the acetal or the aldehyde. In one subclass of this class, the yield of the separated enol ether is greater than 90%, based on the acetal or the aldehyde.

The enol ether can be separated in step (2) by distillation. In one class of this embodiment, in step (2) the enol ether is separated by distillation. The temperature at which the distillation is carried out in step (2) can be lowered by reducing the pressure at which the distillation is carried out. In one subclass of this class, the pressure at which the distillation is carried out is from about 90 kPa to about 0.1 kPa. In one subclass of this class, pressure at which the distillation is carried out is from about 70 kPa to about 0.1 kPa. In one subclass of this class, the pressure at which the distillation is carried out is from about 50 kPa to about 0.1 kPa. In one subclass of this class, the pressure at which the distillation is carried out is from about 30 kPa to about 0.1 kPa. In one subclass of this class, the pressure at which the distillation is carried out is from about 10 kPa to about 0.1 kPa. In one subclass of this class, the pressure at which the distillation is carried out is from about 5 kPa to about 0.1 kPa. In one subclass of this class, the pressure at which the distillation is carried out is from about 3 kPa to about 0.1 kPa. In one subclass of this class, the pressure at which the distillation is carried out is from about 2 kPa to about 0.1 kPa. In one subclass of this class, the pressure at which the distillation is carried out is from about 1 kPa to about 0.1 kPa.

In one subclass of this class, the distillation to separate the enol ether is carried out at a temperature range of from about 50° C. to about 300° C., and at a pressure of from about 101.3 kPa to about 0.1 kPa. In one sub-subclass of this subclass, the distillation to separate the enol ether is carried out at a temperature range of from about 80° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa. In one sub-subclass of this subclass, the distillation to separate the enol ether is carried out at a temperature range of from about 100° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa. In one sub-subclass of this subclass, the distillation to separate the enol ether is carried out at a temperature range of from about 120° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa. In one sub-subclass of this subclass, the distillation to separate the enol ether is carried out at a temperature range of from about 150° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa.

In one sub-subclass of this subclass, the distillation to separate the enol ether is carried out at a temperature range of from about 200° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa.

In one class of this embodiment, in step (2) the enol ether is separated by removing the enol ether from the reaction vessel.

In one class of this embodiment, in step (2) the by-products or unreacted reagents (ex, excess alcohol and aldehyde or acetal) of the reaction can first be separated from the reaction mixture by distillation, followed by: (1) the enol ether being separated by distillation, or (2) the enol ether is removed from the reaction vessel without distillation. In one subclass of this class, the distillation to separate the enol ether is carried out at a temperature range of from about 50° C. to about 300° C., and at a pressure of from about 101.3 kPa to about 0.1 kPa. In one sub-subclass of this subclass, the distillation to separate the enol ether is carried out at a temperature range of from about 80° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa. In one sub-subclass of this subclass, the distillation to separate the enol ether is carried out at a temperature range of from about 100° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa. In one sub-subclass of this subclass, the distillation to separate the enol ether is carried out at a temperature range of from about 120° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa. In one sub-subclass of this subclass, the distillation to separate the enol ether is carried out at a temperature range of from about 150° C. to about 300° C. In one sub-subclass of this subclass, the distillation to separate the enol ether is carried out at a temperature range of from about 200° C. to about 300° C. In one sub-sub-subclass of this sub-class, the distillation to separate the enol ether is carried out at a pressure from about 10 kPa to about 0.1 kPa. In one sub-sub-subclass of this sub-class, the distillation to separate the enol ether is carried out at a pressure from about 1 kPa to about 0.1 kPa.

In one sub-subclass of this subclass, the by-products or unreacted reagents is separated by distillation at a temperature in the range of from about 110° C. to about 185° C., and the enol ether is separated at a temperature of from about 185° C. to about 300° C.

In one embodiment, the process is a process for preparing an enol ether which comprises: (1) reacting: (i) an acetal; or (ii) an alcohol, and an aldehyde; in the presence of a catalyst represented by Formula IV:

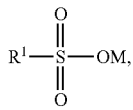
I wherein: $R^1$ is (1) $(C_{1-20})$alkyl, (2) $(C_{3-8})$cycloalkyl, or (3) a 6- to 9-membered aryl, unsubstituted or substituted by 1- to 5 $(C_{1-20})$alkyl substituents; M is an alkaline metal cation, wherein the reaction is carried out at a temperature range of from about 50° C. to about 300° C., wherein the catalyst of Formula IV is present from about 0.01 to about 20 mol % based on 100 mole % of the aldehyde or the acetal; and (2) separating the enol ether, wherein the enol ether has a Gardner color of less than 2 as measured according to ASTM D 1544, and wherein the yield of the separated enol ether is greater than 70%, based on the acetal or the aldehyde.

In one class of this embodiment, step (1) further comprises 0.01 to about 50 mole % of an acid, based on the catalyst of Formula IV. In one subclass of this class, the acid is the conjugate acid of the catalyst of Formula IV.

In one class of this embodiment, step (1) further comprises 0.01 to about 0.1 mole % of an acid, based on the catalyst of Formula IV. In one subclass of this class, the acid is the conjugate acid of the catalyst of Formula IV.

In one embodiment, the enol ether is the compound of Formulas I, II, or III.

In one class of this class, the alcohol is $R^{1a}$OH, $R^{1b}$OH, or HO—$R^{1c}$—OH and the aldehyde is

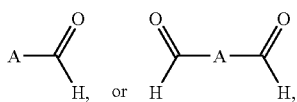

or the acetal is

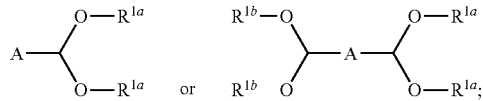

each A is independently (a)

wherein ** indicates the point of attachment, (b) $(C_{3-8})$cycloalkyl, (c) $(C_{3-12})$alkyl,
each $R^{1a}$ or $R^{1b}$ is independently

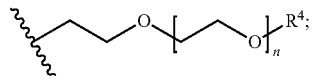

$R^{1c}$ is independently

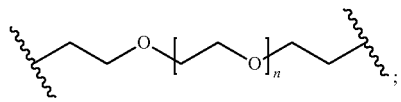

each $R^2$ is independently $(C_{2-12})$alkyl;
each $R^3$ is independently $(C_{1-12})$alkyl;
each $R^4$ is independently hydrogen, $(C_{1-12})$alkyl, $(C_{2-12})$alkenyl, or —C(O)$R^5$;
each $R^5$ is independently $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is independently $(C_{1-4})$alkoxy, or oxo; and
each n is independently an integer from 1 to 15.

In one class of this embodiment, the enol ether is the compound of Formula I.

In one class of this class, the alcohol is $R^{1a}$OH, and the aldehyde is

or the acetal is

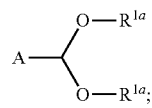

each A is independently (a)

wherein ** indicates the point of attachment, (b) $(C_{3-8})$cycloalkyl, (c) $(C_{3-12})$alkyl,
each $R^{1a}$ is independently

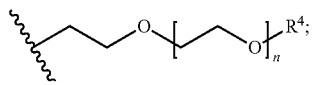

$R^2$ is independently $(C_{2-12})$alkyl;
$R^3$ is independently $(C_{1-12})$alkyl;
each $R^4$ is independently hydrogen, $(C_{1-12})$alkyl, $(C_{2-12})$alkenyl, or —C(O)$R^5$;

each $R^5$ is independently $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;

each $R^6$ is independently $(C_{1-4})$alkoxy, or oxo; and each n is independently an integer from 1 to 15.

In one class of this embodiment, the enol ether is the compound of Formula II.

In one class of this class, the alcohol is $R^{1a}OH$, $R^{1b}OH$, or $HO-R^{1c}-OH$ and the aldehyde is

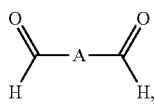

or the acetal is

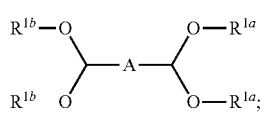

each A is independently $(C_{3-8})$cycloalkyl, or $(C_{3-12})$alkyl, each $R^{1a}$ or $R^{1b}$ is independently

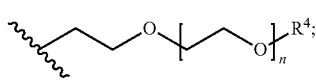

each $R^4$ is independently hydrogen, $(C_{1-12})$alkyl, $(C_{2-12})$alkenyl, or $-C(O)R^5$; each $R^5$ is independently $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl; each $R^6$ is independently $(C_{1-4})$alkoxy, or oxo; and each n is independently an integer from 1 to 15.

In one class of this embodiment, the enol ether is the compound of Formula III.

In one class of this class, the alcohol is $HO-R^{1c}-OH$ and the aldehyde is

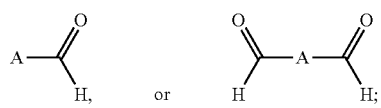

each A is independently (a)

wherein ** indicates the point of attachment, (b) $(C_{3-8})$cycloalkyl, (c) $(C_{3-12})$alkyl, $R^{1c}$ is independently

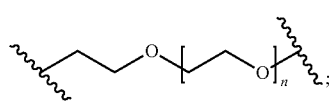

each $R^2$ is independently $(C_{2-12})$alkyl; each $R^3$ is independently $(C_{1-12})$alkyl; and n is independently an integer from 1 to 15.

EXAMPLES

This invention can be further illustrated by the following examples thereof, although it will be understood that these examples are included merely for purposes of illustration and are not intended to limit the scope of the invention unless otherwise specifically indicated.

Abbreviations mL is milliliter; wt % is weight percent; eq is equivalent(s); hrs or h is hour(s); mm is millimeter; m is meter; GC is gas chromatography; ° C. is degree Celsius; min is minute; $t_R$ is retention time; Et is ethyl; J is coupling constant; H is hydrogen; 1H is proton; NMR is nuclear magnetic resonance; MHz is megahertz; DMSO-d6 is hexadeuterated dimethyl sulfoxide; t is triplet; mult is multiplet; d is doublet; Hz is hertz; MPEG is methyl polyethylene glycol; p-TSA is p-toluene sulfonic acid; g is gram; mmol is millimole; mol is mole; kg is kilogram; L is liter; Bu is butyl; Pr is propyl; MeP is methyl palmitate; w/v is weight/volume; μL is microliter; Tg is glass transition temperature; MFFT is minimum film-forming temperature; phr is parts per hundred resin; MW is molecular weight.

Method 1: Preparation of (E/Z)-16-ethyl-5,8,11,14-tetraoxaicos-15-ene 1a

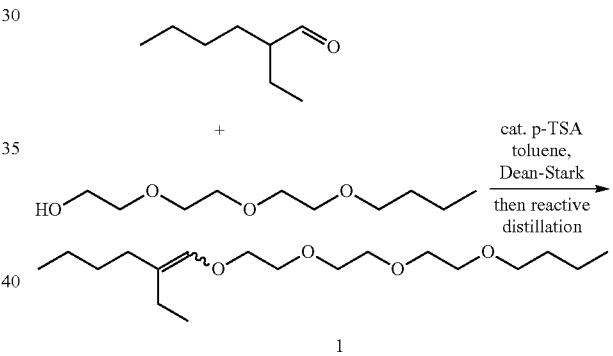

To a 4-necked 3 L round bottom flask fitted with overhead stirrer, thermocouple, and Dean-Stark trap was added 126 g of 2-ethyl hexanal that had been freshly distilled. Then 603 g of triethyleneglycol mono-butylether was charged to the flask, followed by 975 mL of toluene. After adding 9.27 g of p-toluenesulfonic acid monohydrate, the reaction was heated to reflux for 22 hrs. During this time, ca. 16.5 mL of water collected. The reaction mixture was cooled to ambient temperature. The mixture was transferred to a 3 L separatory funnel and then washed with 500 mL of saturated $NaHCO_3$. The layers were allowed to separate. The organics were dried with a small amount of $MgSO_4$. After filtration, the volatiles were stripped under reduced pressure using a rotary evaporator. 5.00 g of sodium xylene sulfonate was added to the crude mixture to serve as a catalyst for the formation of the enol ether. The mixture was then distilled at 5 mm Hg. The excess triethyleneglycol monobutylether was first removed by heating the pot to 185° C. and gradually increasing the temperature to 225° C. (vapor temperature fluctuated between 143-145° C. during the initial phase of the distillation). Once at 225° C., the vapor temperature increased to 184° C., indicating the presence of the product in the distillation head. The pot was further heated to 240°

C. to complete the distillation. The product enol ether was isolated as a mixture of E/Z isomers and was a near colorless liquid. GC-MS tR: 24.31 min (MW=316) and 24.34 min (MW=316). Minor byproduct was determined to be 2-(2-(2-butoxyethoxy)ethoxy)ethyl 2-ethylhexanoate 24.95 min (MW=332). Area % GC tR: 10.58 min and 10.69 min (98.5% enol ether), 10.88 min (1.5% ester byproduct). *Note: "Aged" 2-ethylhexanal (or aldehydes in general) that was exposed to air over time had higher levels of 2-ethylhexanoic acid. Without distillation, using this aged aldehyde with higher levels of acid led to higher levels of the ester byproduct in the final product mixture.

Examples 1b-1c were prepared according to the synthetic procedure of Example 1a.

Example 1b

The product enol ether was isolated as a mixture of E/Z isomers and was a near colorless liquid (Gardner color: 0.10). GC-MS $t_R$: 24.31 min (MW=316) and 24.34 min (MW=316). Minor byproduct was determined to be 2-(2-(2-butoxyethoxy)ethoxy)ethyl 2-ethylhexanoate 24.95 min (MW=332). Area % GC $t_R$: 10.58 min and 10.69 min (95.8% enol ether), 10.88 min (4.20% ester byproduct).

Example 1c

The product enol ether was isolated as a mixture of E/Z isomers and was a near colorless liquid. GC-MS tR:24.31 min (MW=316) and 24.34 min (MW=316). Minor byproduct was determined to be 2-(2-(2-butoxyethoxy)ethoxy) ethyl 2-ethylhexanoate 24.95 min (MW=332). Area % GC tR: 10.58 min and 10.69 min (92.7% enol ether), 10.88 min (7.30% ester byproduct).

Method 2: Alternative Acid-Catalyzed Preparation of (E/Z)-16-ethyl-5,8,11,14-tetraoxaicos-15-ene (Example 1d)

To a 4-necked 2 L round bottom flask fitted with overhead stirrer, thermocouple, and Dean-Stark trap was added 100 g of 2-ethyl hexanal that had been freshly distilled. Then 483 g of triethyleneglycol mono-butylether was charged to the flask, followed by 800 mL of toluene. After adding 7.42 g of p-toluenesulfonic acid monohydrate, the reaction was heated to reflux for 20 hrs. During this time, ca. 13 mL of water collected. The reaction mixture was cooled to ambient temperature. The volatiles were stripped using a rotary evaporator. The crude mixture was then distilled at 3-5 mm Hg following the distillation conditions used in Ex 1a. The product was isolated as a yellow liquid (Gardner color: 2.2) and matched the GC analytical as described in Ex 1a but with additional unknown impurities.

Method 3: Alternative Sodium Sulfonate—Catalyzed Preparation of (E/Z)-16-ethyl-5,8,11,14-tetraoxaicos-15-ene (Example 1e)

To a 4-necked 500 mL round bottom flask fitted with an overhead stirrer, thermocouple, and Dean-Stark trap was added 22.0 g of 2-ethylhexanal, 70.8 g of triethyleneglycol monobutylether, 3.33 g of sodium xylene sulfonate, and 50 g of m-xylene. The reaction was heated to 175° C. to achieve a steady reflux. After 10 hrs, ca. 1 mL of water was collected. The mixture was cooled to ambient temperature and then analyzed by GC to show that the reaction was 50% converted based on aldehyde (Gardner color of distillation pot: 0).

Method 4: Alternate Sodium Sulfonate—Catalyzed Preparation of (E/Z)-16-ethyl-5,8,11,14-tetraoxaicos-15-ene (Example 1f)

To a 4-necked 3 L round-bottom flask fitted with overhead stirrer, thermocouple, and Dean-Stark trap was added 200 g of new 2-ethyl hexanal. Then 644 g of triethyleneglycol mono-butylether was charged to the flask, followed by 250 g of toluene. After adding sodium methanesulfonate (9.21 g, 0.078 mol) and methanesulfonic acid (0.75 g, 0.0078 mol), the reaction mixture was heated to reflux (14 h). During this time, ca. 20 mL of water collected, and $^1$H NMR analysis indicated 70% conversion of the aldehyde. The reactor contents were cooled to 60° C. and 0.499 g of 50% sodium hydroxide in water was added to adjust the ratio of sodium salt:acid. The volatiles were stripped under mild vacuum by placing a short-path condenser on the reaction flask. The mixture was then distilled at 5 mm Hg as previously described. The product enol ether was isolated as a mixture of E/Z isomers and was a near colorless liquid. Isolated yield: 67%. GC-MS tR:24.31 min (MW=316) and 24.34 min (MW=316). Minor byproduct was determined to be 2-(2-(2-butoxyethoxy)ethoxy)ethyl2-ethylhexanoate 24.95 min (MW=332). Area % GC tR:10.58 min and 10.69 min (94.7% enol ether), 10.88 min (5.3% ester byproduct).

The remaining examples were prepared according to Method 1.

Preparation of (E/Z)-16-propyl-5,8,11,14-tetraoxahenicos-15-ene 2

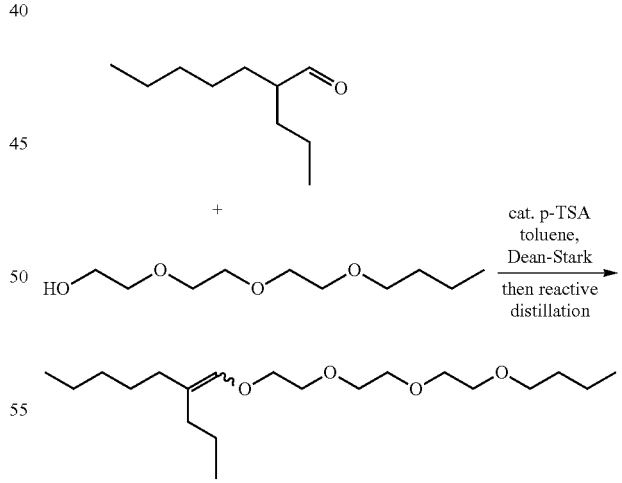

The product enol ether was isolated as a mixture of E/Z isomers and was a near colorless liquid. GC-MS $t_R$: 25.32 min (MW=44) and 25.44 min (MW=344). Minor byproduct was determined to be 2-(2-(2-butoxyethoxy)ethoxy)ethyl 2-propylheptanoate, $t_R$=26.04 min (MW=360). Area % GC $t_R$: 11.23 min and 11.32 min (98.38% enol ether), 11.52 min (1.62% ester byproduct).

41

Preparation of (E/Z)-3-((2-(2-butoxyethoxy)ethoxy)methylene)heptane 3

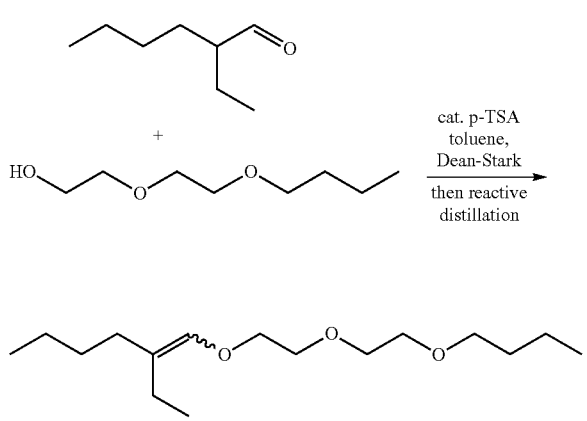

The product enol ether was isolated as a mixture of E/Z isomers and was a near colorless liquid. GC-MS $t_R$: 21.8 min (MW=272) and 21.98 min (MW=272). Minor byproduct was determined to be 2-(2-propoxyethoxy)ethyl 2-ethylhexanoate, $t_R$=22.69 min (MW=288). Area % GC $t_R$: 9.64 min and 9.76 min (97.9% enol ether), 9.97 min (2.10% ester byproduct).

42

Preparation of (E)-16-methyl-5,8,11,14-tetraoxanonadec-15-ene 4

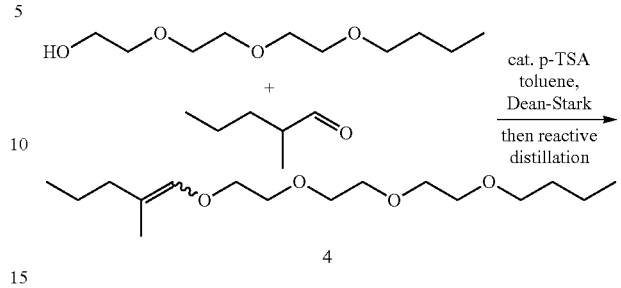

The product enol ether was isolated as a mixture of E/Z isomers and was a near colorless liquid. GC-MS $t_R$: 22.95 min (MW=288) and 23.19 min (MW=288). Minor byproduct was determined to be 2-(2-(2-butoxyethoxy)ethoxy)ethyl 2-methylpentanoate, $t_R$=23.75 min (MW=304). Area % GC $t_R$: 9.83 min and 9.97 min (99.2% enol ether), 10.15 min (0.80% ester byproduct).

Preparation of Example 5, a Mixture of (5E/Z,17E/Z)-5,18-diethyl-7,10,13,16-tetraoxadocosa-5,17-diene 5a and (E/Z)-2-(2-(2-((2-ethylhex-1-en-1-yl)oxy)ethoxy)ethoxy)ethan-1-ol 5b

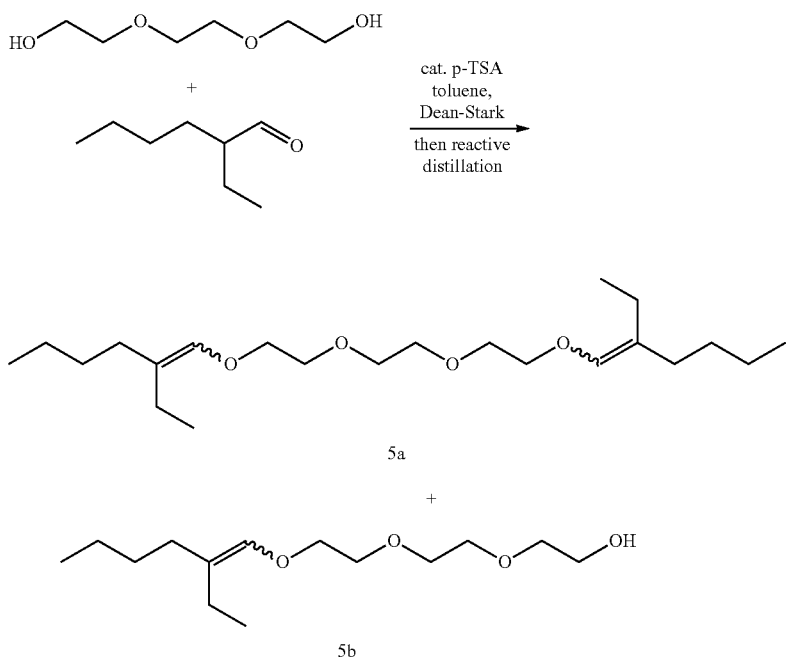

The mixture was isolated as a pale yellow liquid. GC-MS $t_R$: 22.92 min (MW=260) and 23.10 min (MW=260) and 26.32 min (MW=370), 26.48 min (MW=370), and 26.64 min (MW=370). Minor byproduct was determined to be (E/Z)-2-(2-(2-((2-ethylhex-1-en-1-yl)oxy)ethoxy)ethoxy)ethyl 2-ethylhexanoate, $t_R$=27.05 min (MW=386) and 27.19 min (MW=386). Area % GC $t_R$: 9.52 min and 9.65 min (30.30% mono-alcohol), 11.85 min, 11.98 min, and 12.06 min (67.30% bis-enol ether), 12.19 min and 12.27 min (2.40% ester byproduct).

Preparation of Example 6, a Mixture of (5E/Z,17E/Z)-5,18-diethyl-7,10,13,16-tetraoxadocosa-5,17-diene 5a and (E/Z)-2-(2-(2-((2-ethylhex-1-en-1-yl)oxy)ethoxy)ethoxy)ethyl Acetate 6a

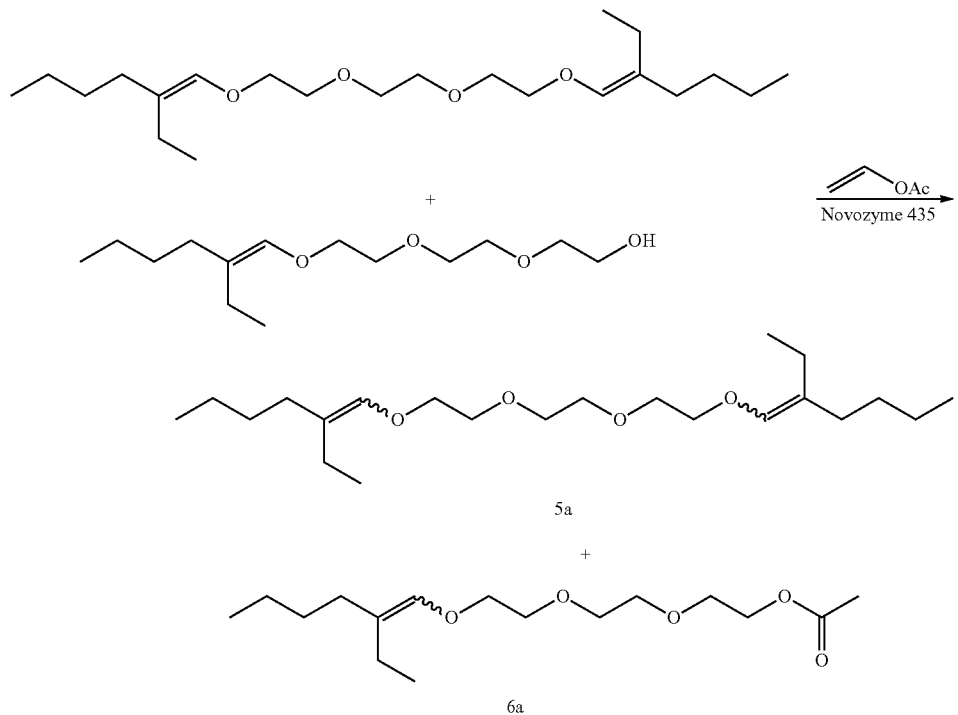

Isolated as a pale yellow liquid. GC-MS $t_R$: 23.97 min (MW=302), 24.13 min (MW=302), 26.32 min (MW=370), 26.48 min (MW=370), and 26.64 min (MW=370). Minor byproduct was determined to be (E/Z)-2-(2-(2-((2-ethylhex-1-en-1-yl)oxy)ethoxy)ethoxy)ethyl 2-ethylhexanoate, $t_R$=27.05 min (MW=386) and 27.19 min (MW=386). Area % GC $t_R$: 10.20 min and 10.28 min (29.82% mono-acetate), 10.84 min, 11.95 min, and 12.03 min (68.18% bis-enol ether), 12.17 min and 12.24 min (2.00% ester byproduct).

Preparation of Example 7, a Mixture of (5E/Z,17E/Z)-5,18-diethyl-7,10,13,16-tetraoxadocosa-5,17-diene 5a and (E/Z)-2-(2-(2-((2-ethylhex-1-en-1-yl)oxy)ethoxy)ethoxy)ethyl Benzoate 7a

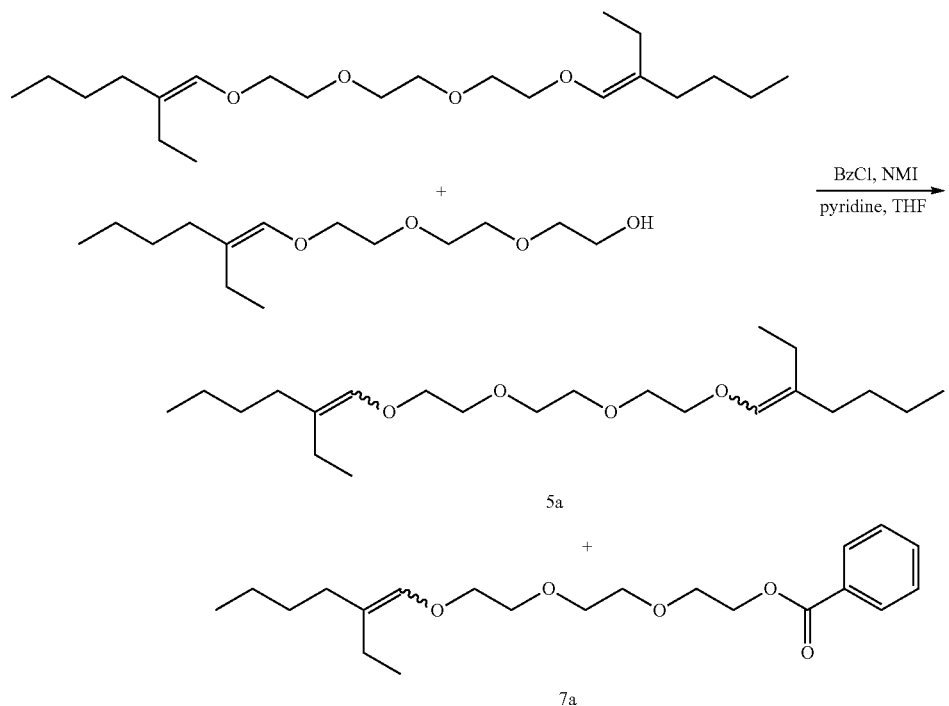

Isolated as a pale yellow liquid. GC-MS $t_R$: 26.34 min (MW=370), 26.49 min (MW=370), 26.62 min (MW=370), 28.39 min (MW=364), and 28.55 min (MW=364). Minor byproduct was determined to be (E/Z)-2-(2-(2-((2-ethylhex-1-en-1-yl)oxy)ethoxy)ethoxy)ethyl 2-ethylhexanoate, $t_R$=27.09 min (MW=386) and 27.23 min (MW=386). Area % GC $t_R$: 11.87 min, 12.00 min, and 12.10 min (73.5% bis-enol ether), 12.21 min and 12.28 min (2.50% ester byproduct), 12.90 min and 13.02 min (24.0% mono-benzoate).

Preparation of Example 8, a Mixture of (5E/Z,20E/Z)-5,21-diethyl-7,10,13,16,19-pentaoxapentacosa-5,20-diene 8a and (E/Z)-14-ethyl-3,6,9,12-tetraoxaoctadec-13-en-1-ol 8b

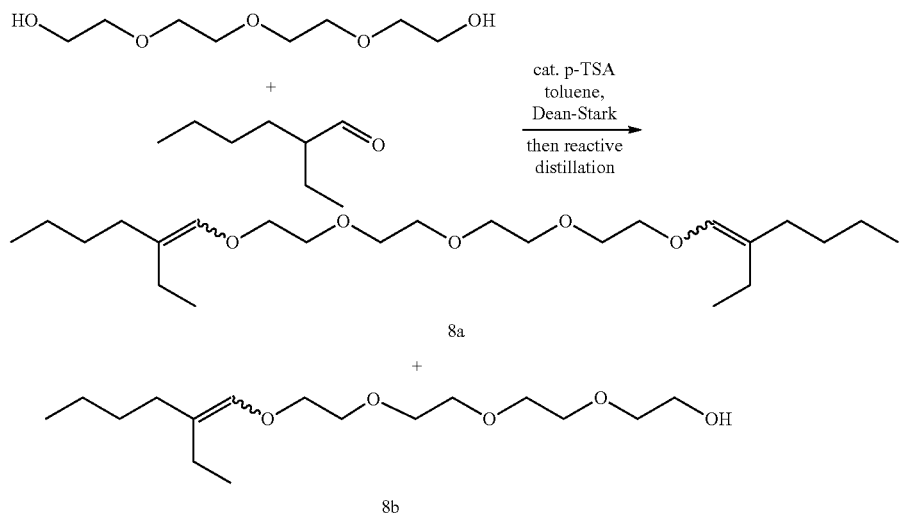

The product mixture was isolated as a near colorless liquid. GC-MS $t_R$: 25.29 min (MW=304), 25.39 min (MW=304), 28.20 min (MW=414), 28.35 (MW=414), and 28.48 min (MW=414). Minor byproduct was determined to be (E/Z)-14-ethyl-3,6,9,12-tetraoxaoctadec-13-en-1-yl 2-ethylhexanoate, $t_R$=28.98 min (MW=430) and 29.14 min (MW=430). Area % GC $t_R$: 10.79 min and 10.90 min (32.5% mono alcohol), 13.09 min, 13.22 min, and 13.31 min (64.6% bis-enol ether), and 13.47 min and 13.59 min (2.90% ester byproduct).

Preparation of 1-cyclohexylidene-2,5,8,11-tetraoxapentadecane 9

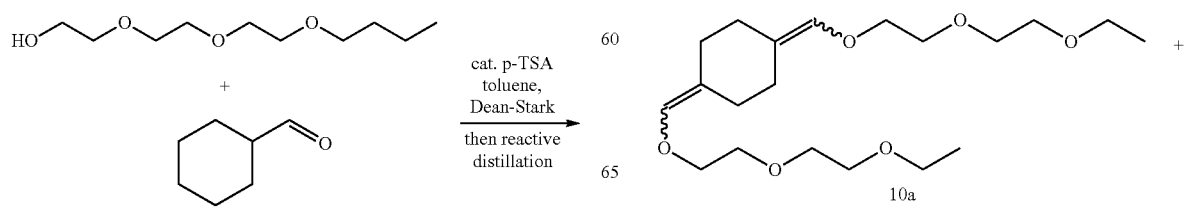

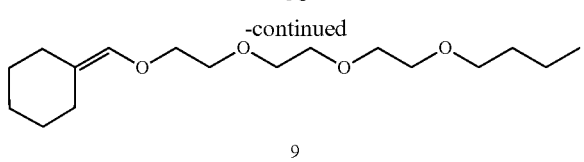

The product enol ether was isolated as a pale yellow liquid. GC-MS $t_R$: 24.94 min (MW=300). Minor byproduct was determined to be 2-(2-(2-butoxyethoxy)ethoxy)ethyl cyclohexanecarboxylate, $t_R$=25.75 min (MW=316). Area % GC $t_R$: 10.99 min (98.0% enol ether), 10.88 min (2.00% ester byproduct).

Preparation of Example 10, a Mixture of (1E/Z,4E/Z)-1,4-bis((2-(2-ethoxyethoxy)ethoxy)methylene)cyclohexane 10a and (1E/Z,3E/Z)-1,3-bis((2-(2-ethoxyethoxy)ethoxy)methylene)cyclohexane 10b

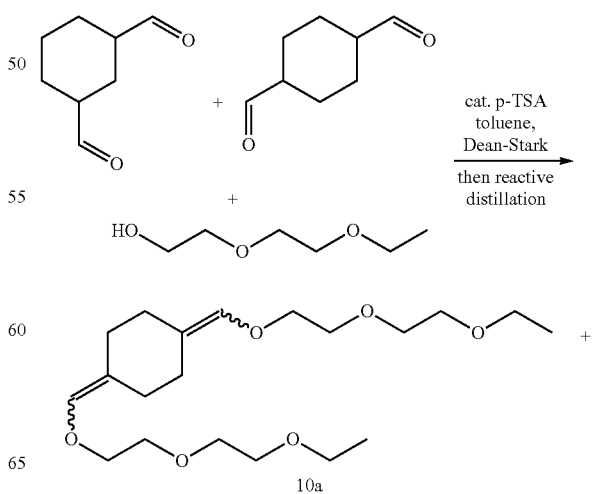

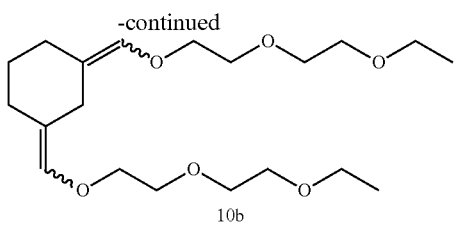

10b

The product mixture was isolated as a pale yellow liquid. GC-MS $t_R$: 27.82 min (MW=372), 28.11 min (MW=372), 28.37 min (MW=372), 28.56 min (MW=372), and 28.60 min (MW=372). Minor byproduct was determined to be a mix of 2-(2-ethoxyethoxy)ethyl 4-((2-(2-ethoxyethoxy) ethoxy)methylene)cyclohexane-1-carboxylate and 2-(2-ethoxyethoxy)ethyl (E/Z)-3-((2-(2-ethoxy-ethoxy)ethoxy) methylene)cyclohexane-1-carboxylate, $t_R$=28.76 min (MW=388), 28.86 min (MW=388), 28.96 min (MW=388), and 29.29 min (MW=388). Area % GC $t_R$: 12.47 min, 12.68 min, 12.87 min, 13.03 min, and 13.07 (97.53% enol ether), 13.11 min, 13.16 min, and 13.31 min (2.47% ester byproducts).

Instrument Parameters—Thermo ISO GCMS

Sample Prep: 100 μL sample diluted to 1 mL with dichloromethane; Column: DB-1701 30 m×0.25 mm×0.25 μm; Oven Ramp: 0-8 mins at 40° C.; Ramp 12 C/min to 280 C, Hold 15 mins; Injector: Temperature—250° C.; Split Flow—150; Carrier Flow Rate—1.5 mL/min; Volume—0.5 μL; MS: Transfer Line—280° C.; Ion Source Temp—250° C.; Mass Range—16-750

Instrument Parameters for Area Percent Determination—Agilent 6890N

Sample Prep: 50 μL sample diluted to 1.5 mL with EtOAc or toluene; Column: DB-5 column 30m×0.25 mm×0.25 μm; Oven Ramp: 3 mins at 100° C.; Ramp 25° C./min to 300° C., Hold 14 mins; Injector: Temperature—240° C.; Carrier Flow Rate—1.5 mL/min; Volume—3 μL.

TABLE 1

Percent VOC Content in Enol Ether Compounds

| Ex. # | % VOC |
|---|---|
| 1a | 0.69 |
| 1b | 0.82 |
| 1c | 0.88 |
| 2 | 1.28 |
| 3 | 100 |
| 4 | 100 |
| 5 | 31.00 |
| 6 | 2.40 |
| 7 | 3.61 |
| 8 | 1.49 |
| 9 | 1.32 |
| 10 | 3.22 |

Volatility Screening (Volatile Organic Compound, VOC): ASTM D6886

GC: Agilent 6890 or equivalent; Column: DB-5 (5% phenyl/95% methylpolysiloxane); 30m×0.25 mm ID×1.00 μm, Agilent Technologies, P/N: 122-5033; Injector: Split/splitless injector, 280° C., Split mode; Carrier Gas: Helium; Column Flow: Constant flow mode, 1.00 mL/minute; Linear Velocity: 25.45 cm/second (at initial oven temperature of 50° C.); Carrier Pressure: 11.96 psi (at initial oven temperature of 50° C.); Total Flow: 53.5 mL/minute; Split Ratio: 50:1; Septum Purge Flow: 2 mL/minute; Detector: Flame Ionization Detector (FID), 280° C.; Detector Gas Flows: Hydrogen: 40 mL/minute; Air: 400 mL/minute; Column+ Makeup (Helium): 45 mL/minute; Oven Program: Initial Temperature: 50° C.; Initial Hold Time: 4 minutes; Program Rate-1: 20° C./minute; Final Temperature-1: 250° C.; Hold Time-1: 6 minutes; Program Rate-2: 20° C./minute; Final Temperature-2: 300° C.; Hold Time-2: 37.5 minutes; Total Run Time: 60 minutes; Data System: EZ-Chrom Elite, Version 3.3.2SP2 or equivalent; Injection Volume: 1.0 μL; Autoinjector: Shimadzu AOC-5000 or equivalent; Rinse Solvent: Acetonitrile;

The internal standard solution used for this method is 1.0265% (w/v) methyl palmitate (MeP) in acetonitrile. It is prepared by accurately weighing 1.0265±0.005 grams of MeP into a 100-mL volumetric flask and diluting to the mark with acetonitrile.

Prior to analyzing samples, a five-point calibration should be performed using Texanol™ standards that reflect the range of expected VOC concentrations (e.g., 1-10%). To prepare Texanol™ calibration standards, first tare a 4-dram vial and cap. Then, add the appropriate amount of Texanol™ for each standard based on a final weight of 0.7000 grams (e.g., 0.0070 grams for a 1% standard). Next, backfill the 4-dram vial with acetonitrile (or other appropriate solvent) until a final weight of 0.7000 is achieved. Add 9.0 mL of acetonitrile (or other suitable solvent), followed by 1000.0 μL of internal standard solution. Cap the vial and vortex thoroughly, then transfer a portion of the solution to a GC vial for injection. Repeat for all desired concentrations. The response factor generated by the Texanol™ calibration is used to quantify all VOCs eluting before methyl palmitate.

A reagent blank, containing all reagents except for the sample or standard, should be run before each set of samples to ensure the chromatographic system is free from interferences. Additionally, it is always prudent to prepare a control standard containing a known concentration of Texanol™ and run it before and after the samples. This is to confirm the validity of the calibration and ensure the instrument is functioning properly. Control standards are prepared like calibration standards, the procedure for which was described previously in this section. Ideally, the concentration of control standards should closely resemble the expected concentrations of VOCs contained in the samples.

Neat coalescent samples were prepared by the following procedure:

1. Accurately weigh 0.7000 grams of sample into a tarred 4-dram vial with screw cap
2. Add 9.0-mL of acetonitrile (or other suitable solvent)
3. Accurately add 1000.0 μL of internal standard solution
4. Cap the vial and vortex thoroughly
5. Transfer a portion of the resulting solution to a GC vial for injection

TABLE 2 phr of coalescent required to lower MFFT to 4.4° C. and 1.67° C. in Rhodoplex ™ SG-30, Acronal ™ 296 D, and Encor ™ 379 model coating systems.

| | Latex | | | | | |
|---|---|---|---|---|---|---|
| | Rhoplex SG-30 | | Acronal 296 D | | Encor 379 | |
| Ex # | 4.4° C. (phr) | 1.67° C. (phr) | 4.4° C. (phr) | 1.67° C. (phr) | 4.4° C. (phr) | 1.67° C. (phr) |
| 1a | 4.16 | 5.24 | 4.84 | 5.91 | 2.21 | 3.61 |
| 1b | 4.04 | 5.09 | 5.26 | 6.38 | 1.76 | 2.87 |
| 1c | 3.89 | 5.10 | 4.85 | 5.92 | 2.33 | 3.86 |
| 2 | 4.31 | 5.41 | 5.31 | 6.44 | 2.52 | 4.18 |

TABLE 2-continued phr of coalescent required to lower MFFT to 4.4° C. and 1.67° C. in Rhodoplex ™ SG-30, Acronal ™ 296 D, and Encor ™ 379 model coating systems.

| | Latex | | | | | |
|---|---|---|---|---|---|---|
| | Rhoplex SG-30 | | Acronal 296 D | | Encor 379 | |
| Ex # | 4.4° C. (phr) | 1.67° C. (phr) | 4.4° C. (phr) | 1.67° C. (phr) | 4.4° C. (phr) | 1.67° C. (phr) |
| 3 | 4.18 | 5.47 | 5.23 | 6.36 | 2.40 | 3.93 |
| 4 | 3.92 | 4.96 | 4.77 | 5.84 | 1.84 | 3.01 |
| 5 | 4.64 | 5.83 | 5.70 | 6.93 | 2.35 | 3.84 |
| 6 | 4.35 | 5.47 | 5.88 | 7.11 | 2.63 | 4.32 |
| 7 | 5.46 | 6.93 | 6.91 | 8.41 | 2.79 | 4.63 |
| 8 | 5.23 | 6.64 | 6.51 | 7.97 | 2.70 | 4.38 |
| 9 | 4.26 | 5.34 | 5.09 | 6.21 | 2.24 | 3.66 |
| 10 | 5.07 | 6.48 | 6.43 | 7.84 | 2.68 | 4.40 |

Minimum Film-Forming Temperature (MFFT) Screening: ASTM D2354-10e

MFFT efficiency testing was based on ASTM D2354. The model instrument used was an MFFT-90 bar which allows samples to be tested from −10° C. to 90° C. For waterborne latexes, reaching a temperature of 2° C. is the primary goal. To reach that temperature, the MFFT bar was set to range from 0° C. to 18° C. This range is important since those Tg values for waterborne latexes somewhat correlate with their coinciding MFFT value. The higher the Tg value, the higher the MFFT value and vice versa. Neat commercial architectural latexes typically lie within this temperature range when testing for MFFT efficiency. Depending on the Tg of the material being tested, the range can be adjusted accordingly to determine the film's MFFT.

The ultimate goal for the final paint is to form a continuous film at a low temperature (2° C.). To achieve this, the MFFT of the neat latex material is first determined. If the neat latex material is above an MFFT of 2° C., we will add coalescent at different phr (% coalescent based on latex solids) levels to allow the latex to reach 20. To reach that temperature, a linear regression of the phr levels is performed. This allows one to determine the appropriate amount of coalescent to add to the final paint formulation.

Test Procedure:
1. Turn water source, MFFT instrument, and nitrogen source on in that order
2. Let MFFT instrument equilibrate ~15 minutes
3. Raise lid on the instrument and place the film caster (~6 WFT) at the cold end (0°) of the bar
4. Our film caster is sectioned into individual squares allowing us to test up to five latex samples at a time
5. Add samples to film caster
6. Draw down samples from cold end to the warm end (18° C.) of the MFFT bar
7. Lower the lid on the instrument
8. Samples will be ready to evaluate in approximately 1-2 hours
9. New MFFT bar instruments are equipped with a cursor. Moving the cursor to the MFFT point of a sample, the temperature value will be shown on a digital display

TABLE 3

Common let-down formulation

| Component | Weight (g) |
|---|---|
| Tronox 826S | 3589.4 |
| TAMOL ™ 165A | 69.4 |
| Water | 1530.1 |
| Triton ™ CF-10 | 20.4 |
| AMP-95 | 20.4 |
| BYK-024 | 25.5 |
| KATHON LX 1.5% | 18.4 |
| Total: | 5273.7 |

TABLE 4

Master Paint Formulations

| | Formulation A | Formulation B | Formulation C | Formulation D | Formulation E |
|---|---|---|---|---|---|
| Common Letdown (g) | 1034.0 | 1034.0 | 1034.0 | 1034.0 | 1034.0 |
| Rhoplex ™ SG-30 (g) | 900.84 | 901.59 | 910.49 | 900.69 | 900.73 |
| Coalescent (g) | Texanol (33.60) | OE400 (34.02) | Ex 1b (27.43) | Ex 6 (31.01) | Ex 8 (36.40) |
| Acrysol ™ RM-6000 (g) | 40.23 | 40.09 | 40.11 | 39.99 | 40.99 |
| Acrysol ™ RM-725 (g) | 13.03 | 12.09 | 14.92 | 10.49 | 23.99 |
| Water | 106.16 | 105.63 | 108.75 | 109.12 | 92.79 |
| Total (g) | 2127.86 | 2127.42 | 2135.70 | 2125.30 | 2128.00 |

TABLE 5

50° C. heat-aged stability of paint formulations

| | Initial | | | 2 Weeks | | | | 4 Weeks | | | |
|---|---|---|---|---|---|---|---|---|---|---|---|
| Formulation | KU | pH | KU | KU | ICI (poise) | pH | KU | KU | ICI (poise) | pH |
| A | 91 | 9.5 | 111 | 20 | 0.998 | | 9.3 | 111 | 20 | 1.008 | 9.3 |
| B | 90 | 9.5 | 111 | 20 | 0.989 | | 9.4 | 109 | 19 | 1.003 | 9.4 |
| C | 92 | 9.4 | 114 | 22 | 1.050 | | 9.4 | 113 | 21 | 1.055 | 9.4 |
| D | 96 | 9.3 | 120 | 24 | 1.237 | | 9.3 | 120 | 24 | 1.181 | 9.2 |
| E | 88 | 9.4 | 105 | 16 | 0.895 | | 9.4 | 104 | 15 | 0.905 | 9.4 |

Stormer viscosities were measured with a KU-2 viscometer by Brookfield. ICI viscosities were measured with a BYK CAP 2000+ viscometer.

TABLE 6

28-day König hardness

| Formulation | Dry Time (1 Day) Konig's Hardness (sec) | Dry Time (7 Days) Konig's Hardness (sec) | Dry Time (28 Days) Konig's Hardness (sec) |
|---|---|---|---|
| A | 13 | 14 | 19 |
| B | 7 | 9 | 9 |
| C | 8 | 9 | 14 |
| D | 9 | 9 | 15 |
| E | 8 | 8 | 9 |

TABLE 7

| | 28-day König hardness (50° C. heat-aged paint formulations) | | |
|---|---|---|---|
| Formulation | Dry Time (1 Day) Konig's Hardness (sec) | Dry Time (7 Days) Konig's Hardness (sec) | Dry Time (28 Days) Konig's Hardness (sec) |
| A | 12 | 14 | 17 |
| B | 8 | 7 | 7 |
| C | 8 | 8 | 13 |
| D | 8 | 9 | 13 |
| E | 6 | 6 | 9 |

Drawdowns of the paints (10 mil wet on glass panels) were prepared for König testing. All drawdowns were stored in a controlled temperature room until use. König testing was done using BYK Gardner pendulum hardness tester.

What is claimed is:

1. A compound according to Formula I:

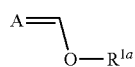  I wherein:
A is
(a)

wherein ** indicates the point of attachment, or
(b) $(C_{3-8})$cycloalkyl;
$R^{1a}$ is

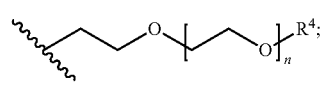

$R^2$ is ethyl, propyl, butyl, or pentyl;
$R^3$ is methyl, ethyl, or propyl;
$R^4$ is hydrogen, $(C_{1-12})$alkyl, $(C_{2-12})$alkenyl, or —C(O)$R^5$;
$R^5$ is $(C_{1-12})$alkyl unsubstituted or substituted by 1-2 $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
n is an integer from 1 to 15.

2. The compound of claim 1, wherein A is (a)

wherein ** indicates the point of attachment.

3. The compound of claim 2, wherein $R^2$ is butyl; and $R^3$ is ethyl.

4. The compound of claim 1, wherein A is $(C_{3-8})$cycloalkyl.

5. The compound of claim 4, wherein A is cyclohexyl.

6. The compound of claim 1, chosen from

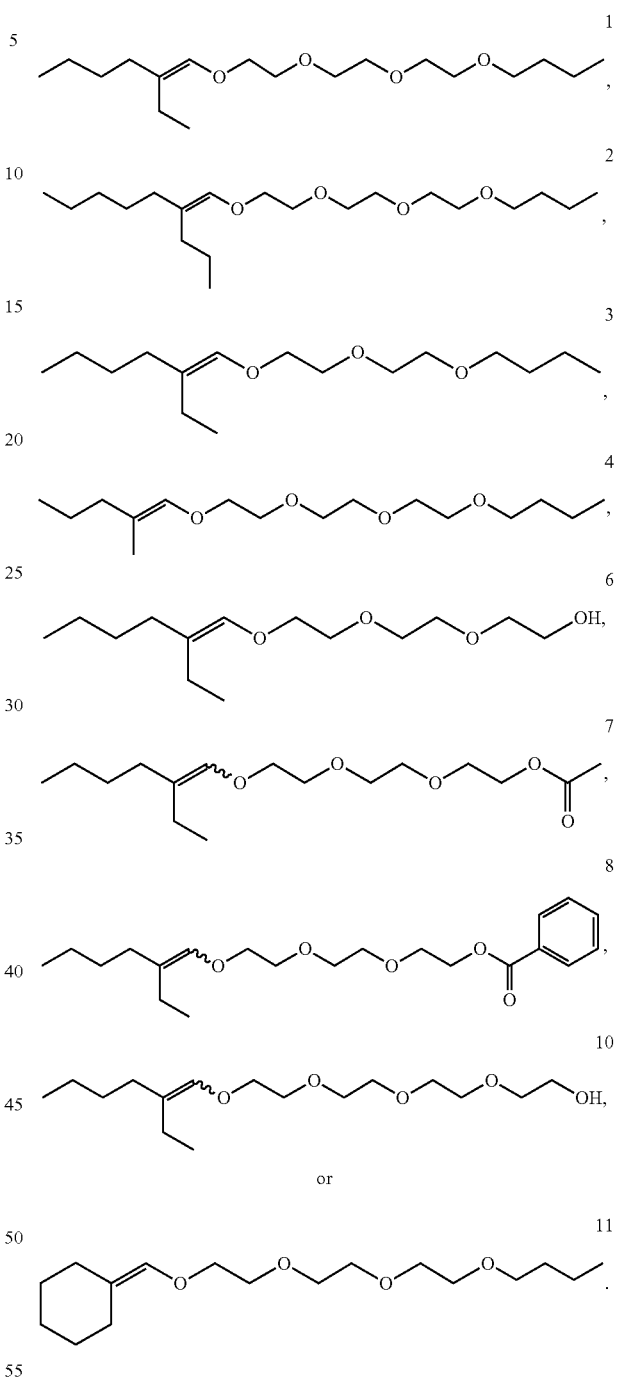

7. The compound of claim 1, wherein the compound of Formula I has a volatile organic content of less than 50 wt % according to ASTM D6886.

8. The compound of claim 1, further comprising a polymer.

9. The compound of claim 8, wherein the polymer is a latex polymer.

10. The compound of claim 8, wherein the compound of Formula I is present from about 1 to about 20 phr relative to the sum total of the polymer.

11. A compound according to Formula II:

$$R^{1b}O\underset{}{\diagup}\overset{A}{=}\underset{}{\diagdown}O—R^{1a}\quad\text{II}$$

wherein:
A is $(C_{3-20})$alkyl or $(C_{3-8})$cycloalkyl;
$R^{1a}$ and $R^{1b}$ are independently

[structure: $\sim\!\!\sim\!\!\sim\!\!-\!\!-\!\!O\!-\!\!\left[\!\!-\!\!-\!\!O\!-\!\!\right]_n\!\!-\!\!R^4$];

each $R^4$ is independently $(C_{1-12})$alkyl, $(C_{2-12})$alkenyl, or —C(O)R$^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

12. The compound of claim 11, wherein A is cyclohexyl.

13. The compound of claim 11, chosen from

[structure 12]

, or

[structure 13]

14. The compound of claim 11, wherein the compound of Formula II has a volatile organic content of less than 50 wt % according to ASTM D6886.

15. The compound of claim 11, further comprising a polymer.

16. The compound of claim 15, wherein the polymer is a latex polymer.

17. The compound of any claim 15, wherein the compound of Formula II is present from about 1 to about 20 phr relative to the sum total of the polymer.

18. A compound according to Formula III:

$$A\!\!=\!\!\diagdown\!\!O—R^{1c}O\!\!\diagup\!\!=\!\!A\quad\text{III}$$

wherein:
each A is independently
(a)

[structure with $R^2$ and $R^3$, ** indicates point of attachment]

wherein ** indicates the point of attachment, or
(b) $(C_{3-8})$cycloalkyl;
$R^{1c}$ is

[structure: $\sim\!\!\sim\!\!-\!\!-\!\!O\!-\!\!\left[\!\!-\!\!-\!\!O\!-\!\!\right]_n\!\!-\!\!\sim\!\!\sim$];

each $R^2$ is independently $(C_{2-12})$alkyl;
each $R^3$ is independently $(C_{1-12})$alkyl; and
n is an integer from 1 to 15.

19. The compound of claim 18, wherein each A is

[structure with $R^2$ and $R^3$, ** indicates point of attachment]

wherein ** indicates the point of attachment.

20. The compound of claim 18, wherein $R^2$ is ethyl, propyl, butyl, or pentyl.

21. The compound of claim 18, wherein $R^3$ is methyl, ethyl, or propyl.

22. The compound of claim 18, wherein $R^2$ is butyl; and $R^3$ is ethyl.

* * * * *